United States Patent
Gray

(10) Patent No.: US 8,868,212 B2
(45) Date of Patent: Oct. 21, 2014

(54) MEDICAL DEVICE WITH AN ELECTRICALLY CONDUCTIVE ANTI-ANTENNA MEMBER

(75) Inventor: Robert W. Gray, Rochester, NY (US)

(73) Assignee: Medtronic, Inc., Minneapolis, MN (US)

( * ) Notice: Subject to any disclaimer, the term of this patent is extended or adjusted under 35 U.S.C. 154(b) by 1804 days.

(21) Appl. No.: 11/214,620

(22) Filed: Aug. 30, 2005

(65) Prior Publication Data

US 2005/0283168 A1 Dec. 22, 2005

Related U.S. Application Data

(63) Continuation of application No. 60/698,393, filed on Jul. 12, 2005.

(51) Int. Cl.

| | | |
|---|---|---|
| *A61N 1/02* | (2006.01) | |
| *A61B 5/02* | (2006.01) | |
| *A61F 2/90* | (2013.01) | |
| *A61F 2/86* | (2013.01) | |
| *A61L 31/12* | (2006.01) | |
| *A61F 2/91* | (2013.01) | |
| *A61N 1/05* | (2006.01) | |
| *A61B 5/00* | (2006.01) | |
| *G01R 33/28* | (2006.01) | |
| *A61N 1/08* | (2006.01) | |
| *A61L 31/18* | (2006.01) | |
| *A61L 31/02* | (2006.01) | |
| *A61B 19/00* | (2006.01) | |
| *A61N 1/37* | (2006.01) | |
| *A61B 5/055* | (2006.01) | |
| *A61N 2/00* | (2006.01) | |

(52) U.S. Cl.
CPC ............ *A61N 1/056* (2013.01); *A61B 5/02007* (2013.01); *A61F 2/90* (2013.01); *A61F 2/86* (2013.01); *A61B 2019/4081* (2013.01); *A61L 31/124* (2013.01); *A61N 1/37* (2013.01); *A61F 2210/009* (2013.01); *A61B 2019/5236* (2013.01); *A61F 2/91* (2013.01); *A61B 5/7203* (2013.01); *G01R 33/285* (2013.01); *A61B 19/40* (2013.01); *A61B 5/055* (2013.01); *A61N 2/00* (2013.01); *A61N 1/08* (2013.01); *A61L 31/18* (2013.01); *A61L 31/022* (2013.01)
USPC .......................................................... 607/119

(58) Field of Classification Search
USPC .......................................................... 607/119
See application file for complete search history.

(56) References Cited

U.S. PATENT DOCUMENTS 2,804,546 A * 8/1957 Wischmeyer .................... 327/44
4,320,763 A 3/1982 Money (Continued)

FOREIGN PATENT DOCUMENTS

WO WO03005898 A1 1/2003
WO WO03015662 2/2003

OTHER PUBLICATIONS

Arno Buecker, et al., "Artifact-Free In-Stent Lumen Visualization by Standard Magnetic Resonance Angiography Using a New Metallic Magnetic Resonance Imaging Stent" Circulation, Apr. 16, 2002,pp. 1772-1775.

(Continued)

*Primary Examiner* — Eric D. Bertram
(74) *Attorney, Agent, or Firm* — Michael J. Ostrom; Stephen W. Bauer

(57) ABSTRACT

A lead includes a conductor having a distal end and a proximal end and a resonant circuit connected to the conductor. The resonant circuit has a resonance frequency approximately equal to an excitation signal's frequency of a magnetic resonance imaging scanner or a resonance frequency not tuned to an excitation signal's frequency of a magnetic resonance imaging scanner so as to reduce the current flow through a tissue area, thereby reducing tissue damage. The resonant circuit may be included in an adapter that provides an electrical bridge between a lead a medical device such as an electrode, sensor, or signal generator. The resonant circuit may also be included directly in the housing of a medical device.

18 Claims, 28 Drawing Sheets

(56) References Cited

U.S. PATENT DOCUMENTS

| | | | |
|---|---|---|---|
| 4,661,530 A | 4/1987 | Gogolewski et al. | |
| 4,830,003 A | 5/1989 | Wolff et al. | |
| 5,133,732 A | 7/1992 | Wiktor | |
| 5,170,802 A | 12/1992 | Mehra | |
| 5,217,010 A * | 6/1993 | Tsitlik et al. | 607/9 |
| 5,235,281 A | 8/1993 | Haragashira et al. | |
| 5,278,503 A | 1/1994 | Keller et al. | |
| 5,320,100 A | 6/1994 | Herweck et al. | |
| 5,423,881 A | 6/1995 | Breyen et al. | |
| 5,507,767 A | 4/1996 | Maeda et al. | |
| 5,630,829 A | 5/1997 | Lauterjung | |
| 5,702,419 A | 12/1997 | Berry et al. | |
| 5,725,572 A | 3/1998 | Lam et al. | |
| 5,727,552 A | 3/1998 | Ryan | |
| 5,824,045 A | 10/1998 | Alt | |
| 5,851,226 A * | 12/1998 | Skubitz et al. | 607/126 |
| 5,860,999 A | 1/1999 | Schnepp-Pesch et al. | |
| 5,897,585 A | 4/1999 | Williams | |
| 6,032,063 A | 2/2000 | Hoar et al. | |
| 6,033,436 A | 3/2000 | Steinke et al. | |
| 6,074,362 A | 6/2000 | Jang et al. | |
| 6,117,167 A | 9/2000 | Goicoechea et al. | |
| 6,123,722 A | 9/2000 | Fogarty et al. | |
| 6,156,064 A | 12/2000 | Chouinard | |
| 6,159,239 A | 12/2000 | Greenhalgh | |
| 6,168,619 B1 | 1/2001 | Dinh et al. | |
| 6,183,508 B1 | 2/2001 | Stinson et al. | |
| 6,183,509 B1 | 2/2001 | Dibie | |
| 6,221,099 B1 | 4/2001 | Andersen et al. | |
| 6,221,100 B1 | 4/2001 | Strecker | |
| 6,221,102 B1 | 4/2001 | Baker et al. | |
| 6,224,625 B1 | 5/2001 | Jayaraman | |
| 6,228,111 B1 | 5/2001 | Törmälä et al. | |
| 6,231,516 B1 | 5/2001 | Keilman et al. | |
| 6,238,491 B1 | 5/2001 | Davidson et al. | |
| 6,241,691 B1 | 6/2001 | Ferrera et al. | |
| 6,251,136 B1 | 6/2001 | Guruwaiya et al. | |
| 6,272,370 B1 | 8/2001 | Gillies et al. | |
| 6,280,385 B1 | 8/2001 | Melzer et al. | |
| 6,325,822 B1 | 12/2001 | Chouinard et al. | |
| 6,350,279 B1 | 2/2002 | McGuinness | |
| 6,393,314 B1 | 5/2002 | Watkins et al. | |
| 6,424,234 B1 * | 7/2002 | Stevenson | 333/182 |
| 6,451,026 B1 | 9/2002 | Biagtan et al. | |
| 6,456,890 B2 | 9/2002 | Pianca et al. | |
| 6,471,645 B1 | 10/2002 | Warkentin et al. | |
| 6,496,006 B1 | 12/2002 | Vrijheid | |
| 6,501,978 B2 | 12/2002 | Wagshul et al. | |
| 6,503,272 B2 | 1/2003 | Duerig et al. | |
| 6,506,972 B1 | 1/2003 | Wang | |
| 6,539,253 B2 | 3/2003 | Thompson et al. | |
| 6,564,084 B2 | 5/2003 | Allred, III et al. | |
| 6,606,513 B2 | 8/2003 | Lardo et al. | |
| 6,628,980 B2 | 9/2003 | Atalar et al. | |
| 6,673,999 B1 | 1/2004 | Wang et al. | |
| 6,675,049 B2 | 1/2004 | Thompson et al. | |
| 6,700,472 B2 | 3/2004 | Wang et al. | |
| 6,701,176 B1 | 3/2004 | Halperin et al. | |
| 6,711,443 B2 | 3/2004 | Osypka | |
| 6,712,844 B2 | 3/2004 | Pacetti | |
| 6,713,671 B1 | 3/2004 | Wang et al. | |
| 6,714,809 B2 | 3/2004 | Lee et al. | |
| 6,745,079 B2 | 6/2004 | King | |
| 6,765,144 B1 | 7/2004 | Wang et al. | |
| 6,767,360 B1 * | 7/2004 | Alt et al. | 623/1.15 |
| 6,815,609 B1 | 11/2004 | Wang et al. | |
| 6,822,548 B2 | 11/2004 | Wang et al. | |
| 6,824,512 B2 | 11/2004 | Warkentin et al. | |
| 6,844,492 B1 | 1/2005 | Wang et al. | |
| 6,846,985 B2 | 1/2005 | Wang et al. | |
| 6,847,837 B1 | 1/2005 | Melzer et al. | |
| 6,864,418 B2 | 3/2005 | Wang et al. | |
| 6,876,886 B1 | 4/2005 | Wang | |
| 6,892,086 B2 | 5/2005 | Russell | |
| 6,898,454 B2 | 5/2005 | Atalar et al. | |
| 6,906,256 B1 | 6/2005 | Wang | |
| 7,013,180 B2 | 3/2006 | Villaseca et al. | |
| 7,048,716 B1 | 5/2006 | Kucharczyk et al. | |
| 2001/0044651 A1 | 11/2001 | Steinke et al. | |
| 2002/0040185 A1 | 4/2002 | Atalar et al. | |
| 2002/0107562 A1 | 8/2002 | Hart et al. | |
| 2002/0111542 A1 | 8/2002 | Warkentin et al. | |
| 2002/0138135 A1 | 9/2002 | Duerig et al. | |
| 2002/0156515 A1 | 10/2002 | Jang et al. | |
| 2002/0161421 A1 | 10/2002 | Lee et al. | |
| 2003/0018369 A1 | 1/2003 | Thompson et al. | |
| 2003/0036776 A1 | 2/2003 | Foster et al. | |
| 2003/0050557 A1 * | 3/2003 | Susil et al. | 600/424 |
| 2003/0083723 A1 | 5/2003 | Wilkenson et al. | |
| 2003/0083726 A1 | 5/2003 | Zeijlemaker et al. | |
| 2003/0088178 A1 | 5/2003 | Owens et al. | |
| 2003/0105509 A1 | 6/2003 | Jang et al. | |
| 2003/0120148 A1 | 6/2003 | Pacetti | |
| 2003/0135114 A1 | 7/2003 | Pacetti et al. | |
| 2003/0135268 A1 | 7/2003 | Desai | |
| 2003/0171670 A1 | 9/2003 | Gumb et al. | |
| 2003/0199768 A1 | 10/2003 | Cespedes et al. | |
| 2004/0077995 A1 | 4/2004 | Ferek-Petric et al. | |
| 2004/0078067 A1 | 4/2004 | Thompson et al. | |
| 2004/0138733 A1 | 7/2004 | Weber et al. | |
| 2004/0158310 A1 | 8/2004 | Weber et al. | |
| 2004/0164836 A1 | 8/2004 | Wang et al. | |
| 2004/0176822 A1 | 9/2004 | Thompson et al. | |
| 2004/0181177 A1 | 9/2004 | Lee et al. | |
| 2004/0210289 A1 | 10/2004 | Wang et al. | |
| 2004/0225213 A1 | 11/2004 | Wang et al. | |
| 2004/0249428 A1 | 12/2004 | Wang et al. | |
| 2004/0249440 A1 | 12/2004 | Bucker et al. | |
| 2004/0263172 A1 | 12/2004 | Gray et al. | |
| 2004/0263173 A1 | 12/2004 | Gray | |
| 2004/0263174 A1 | 12/2004 | Gray et al. | |
| 2005/0029990 A1 * | 2/2005 | Tsukamoto et al. | 320/135 |
| 2005/0043761 A1 | 2/2005 | Connelly et al. | |
| 2005/0155779 A1 | 7/2005 | Wang et al. | |
| 2005/0197677 A1 | 9/2005 | Stevenson | |
| 2005/0222642 A1 | 10/2005 | Przybyszewski et al. | |
| 2005/0222647 A1 | 10/2005 | Wahlstrand et al. | |
| 2005/0222656 A1 | 10/2005 | Wahlstrand et al. | |
| 2005/0222657 A1 | 10/2005 | Wahlstrand et al. | |
| 2005/0222658 A1 | 10/2005 | Hoegh et al. | |
| 2005/0222659 A1 | 10/2005 | Olsen et al. | |
| 2006/0118319 A1 | 6/2006 | Wang et al. | |
| 2006/0136039 A1 | 6/2006 | Martin | |
| 2006/0247684 A1 | 11/2006 | Halperin et al. | |
| 2006/0247747 A1 | 11/2006 | Olsen et al. | |
| 2006/0247748 A1 | 11/2006 | Wahlstrand et al. | |
| 2006/0282153 A1 | 12/2006 | Jang | |

OTHER PUBLICATIONS

Lambertus W. Bartels et al., "MR Imaging of Vascular Stents: Effects of Susceptibility, Flow, and Radiofrequency Eddy Currents," published in Journal of Vascular and Interventional Radiology, vol. 12, No. 3, Mar. 2001, pp. 365-371.

Lambertus W. Bartels, et al., "Improved Lumen Visualization in Metallic Vascular Implants by Reducing RF Artifacts," published in Magnetic Resonance in Medicine, 74:171-180 (2002).

Robert C. Susil, et al., Multifunctional Interventional Devices for MRI: A Combined Electrophysiology/MRI Catheter, Magnetic Resonance in Medicine, Feb. 20, 2002, vol. 47.

Adam, M.D., et al., Interventional Magnetic Resonance Angiography, Seminars in Interventional Radiology, vol. 16, No. 1, 1991, at 31-37.

Amano, M.D., et al., Metallic Artifacts of Coronary and Iliac Arteries Stents in MRI Angiography and Contrast-Enhanced CT, Clinical Imaging, vol. 23, No. 2, Mar./Apr. 1999, at 85-89.

Bakker, et al., MR-Guided Balloon Angioplasty: In Vitro Demonstration of the Potential of MRI for Guiding Monitoring, and Evaluating Endovascular Interventions, JMRI, vol. 8, Jan./Feb. 1998, at 245-250.

CDRH Magnetic Resonance Working Group, A Primer on Medical Device Interactions With Magnetic Resonance Imaging Systems, http://www.fda.gov/cdrh/ode/ primerf6.html, Mar. 5, 2000, at 1-18.

(56) References Cited

OTHER PUBLICATIONS

Colombo, M.D., et al., Biodegradable Stents "Fulfilling the Mission and Stepping Away" Circulation 2000, Jul. 25, 2000, 202:371-373 http://www.circulationaha.org.

De Cobelli, et al., MRI Assessment of Coronary Stents Valutazione RMDelgi Stent Coronarici, RAYS, vol. 24, No. 1, 1999 at 140-148.

Duerinckx, M.D., et al., Assessment of Coronary Artery Patency After Stent Placement Using Magnetic Resonance Angiography, JMRI, vol. 8, No. 4, Jul./Aug. 1998, at 896-902.

Friedrich, et al., Behavior of Implantable Coronary Stents During Magnetic Resonance Imaging, International Journal of Cardiovascular Interventions, vol. 2, at 217-222, Jun. 27, 2006.

Girard, et al., Wallstent Metallic Biliary Endoprosthesis: MR Imaging Characteristics, Radiology, vol. 184, No. 3, at 874-876.

Hilfiker, M.D, et al., Plain and Covered Stent-Grafts: In Vitro Evaluation of Characteristics At Three Dimensional MR Angiography, Radiology, vol. 211, No. 3, Jun. 1999, at 693-697.

Hug, M.D. et al., Cornary Arterial Stents: Safety and Arifacts During MR Imagining, Radiology 2000, vol. 216, Nov. 3, at 781-787.

Kee, M.D., et al, MR-Guided Transjugular Portosystemic Shunt Placement in a Swine Model, JVIR, vol. 10, No. 5, May 1999, at 529-535.

Laissy, et al., Magnetic Resonance Angiography of Intravascular Endoprotheses: Investigation of Three Devices, Cardiovascular and Interventional Radiology, vol. 18, 1995, at 360-366.

Lardo, Ph.D., Real-Time Magnetic Resonance Imagining: Diagnostic and Interventional Applications, Pediatric Cardiology vol. 21, 2000, at 80-98.

Lenhart, M.D., et al., Stent Appearance at Contrast-Enhanced MR Angiography: In Vitro Examination with 14 Stents, Radiology Oct. 2000, vol. 271, No. 1, at 173-178.

Lufkin, et al., Interventional MRI: Update, European Radiology, vol. 7, (Suppl. 5), 1997 at 187-200.

Manke,C.; Stentagioplastie von Beckenarterienstenosen unter MRI-Kontrolle: Erste klinische Ergebnisse, Fotschr Rontgenstr, 2000:172, at 92-97.

Manke, MD, et al.; Magnetic Resonance Monitoring of Stent Deployment in Vitro Evaluation of Different Stent Designs and Stent Delivery Systems, Investigative Radiology, vol. 35, No. 6, Jun. 2000, at 343-351.

Matsumoto,et al.; Gadolinium Enhanced MR Imagining of Vascular Stents, Journal of Computer Assisted Tomography, vol. 14, No. 3, May/Jun. 1990, at 357-361.

Matsumoto, et al., Tantalum Vascular Stents: In Vivo Evaluation With MR Imagining, Radiology, vol. 170, No. 3, Mar. 1989, at 753-755.

Nitatori, et al., MRI Artifacts of Metallic Stents Derived From Imaging Sequencing and the Ferromagnetic Nature of Materials, Radiation Medicine, vol. 17, No. 4, 1999, at 329-334.

Omary, M.D. et al, MR-Guided Angioplasty of Renal Artery Stenosis in a Pig Model: A Feasibility Study, J. JVIR 2000; vol. 11, at 373-381.

Schenck, The Role of Magnetic Susceptibility in Magnetic Resonance Imaging: MRI Magnetic Compatibility of the First and Second Kinds, Medical Physics, vol. 23, No. 6, Jun. 1996, at 815-850.

Shellock, Metallic Stents: Evaluation of MR Imaging Safety, AIR, vol. 173, Sep. 1999, at 543-547.

Strom, et al., Safety of Implantable Coronary Stents During 1 H-Magnetic Resonance Imaging at 1.0 and 1.5 T, Journal of Cardiovascular Magnetic Resonance vol. I , No. 3, 1999, at 239-245.

Stroman, et al., Will It Be Feasible to Insert Endoprostheses Under Interventional MRI?, J Endovasc-Surg, vol. 3, 1996, at 396-404.

Taal, et al., Potential Risks and Artifacts of Magnetic Resonance Imaging of Self-Expandable Esophageal Stents, Gastrointestinal Endoscopy, vol. 46, No. 5, 1997, at 424-429.

Tamai, M.D. et al., Initial and 6-Month Results of Biodegradable Poly-I-Lactic Acid Coronary Stents In Humans, Circulation, Jul. 25, 2000, at 399-404 http://www.circulationaha.org.

Tamai, M.D., et al., A Biodegradable Poly-I-Lactic Acid Coronary Stent in the Porcine Coronary Artery, Journal of Interventional Cardiology, vol. 12, No. 6, 1999 at 443-449.

Tsuji, MD, et al, Experimental and Clinical Studies of Biodegradable Polymeric Stents, Journal of Interventional Cardiology, vol. 13, Nov. 6, 2000, at 439-445.

Wendt,et al., Visualisation, Tracking and Navigation of Instruments for MN-Guided Interventional Procedures, Min Invas Ther & Allied Technol, vol. 8, No. 5, at 317-326, Jun. 27, 2006.

\* cited by examiner

MEDICAL DEVICE WITH AN ELECTRICALLY CONDUCTIVE ANTI-ANTENNA MEMBER

PRIORITY INFORMATION

The present application claims priority, under 35 U.S.C. §119(e), from U.S. Provisional Patent Application, Ser. No. 60/698,393, filed on Jul. 12, 2005. The entire content of U.S. Provisional Patent Application, Ser. No. 60/698,393, filed on Jul. 12, 2005, is hereby incorporated by reference.

FIELD OF THE PRESENT INVENTION

The present invention relates generally to a medical device that includes an anti-antenna device to prevent or significantly reduce damaging heat, created by currents or voltages induced by outside electromagnetic energy, to a tissue area. More particularly, the present invention is directed to a medical device that includes an anti-antenna device to prevent or significantly reduce damaging heat, created by currents or voltages induced by magnetic-resonance imaging, to a tissue area.

BACKGROUND OF THE PRESENT INVENTION

Magnetic resonance imaging has been developed as an imaging technique adapted to obtain both images of anatomical features of human patients as well as some aspects of the functional activities of biological tissue. These images have medical diagnostic value in determining the state of the health of the tissue examined.

In a magnetic-resonance imaging process, a patient is typically aligned to place the portion of the patient's anatomy to be examined in the imaging volume of the magnetic-resonance imaging apparatus. Such a magnetic-resonance imaging apparatus typically comprises a primary magnet for supplying a constant magnetic field ($B_0$) which, by convention, is along the z-axis and is substantially homogeneous over the imaging volume and secondary magnets that can provide linear magnetic field gradients along each of three principal Cartesian axes in space (generally x, y, and z, or $x_1$, $x_2$ and $x_3$, respectively). A magnetic field gradient ($\Delta B_0/\Delta x_i$) refers to the variation of the field along the direction parallel to $B_0$ with respect to each of the three principal Cartesian axes, $x_i$. The apparatus also comprises one or more radio-frequency coils which provide excitation signals to the patient's body placed in the imaging volume in the form of a pulsed rotating magnetic field. This field is commonly referred to as the scanner's "B1" field and as the scanner's "RF" or "radio-frequency" field. The frequency of the excitation signals is the frequency at which this magnetic field rotates. These coils may also be used for detection of the excited patient's body material magnetic-resonance imaging response signals.

The use of the magnetic-resonance imaging process with patients who have implanted medical assist devices; such as cardiac assist devices or implanted insulin pumps; often presents problems. As is known to those skilled in the art, implantable devices (such as implantable pulse generators and cardioverter/defibrillator/pacemakers) are sensitive to a variety of forms of electromagnetic interference because these enumerated devices include sensing and logic systems that respond to low-level electrical signals emanating from the monitored tissue region of the patient. Since the sensing systems and conductive elements of these implantable devices are responsive to changes in local electromagnetic fields, the implanted devices are vulnerable to external sources of severe electromagnetic noise, and in particular, to electromagnetic fields emitted during the magnetic resonance imaging procedure. Thus, patients with implantable devices are generally advised not to undergo magnetic resonance imaging procedures.

To more appreciate the problem, the use of implantable cardiac assist devices during a magnetic-resonance imaging process will be briefly discussed.

The human heart may suffer from two classes of rhythmic disorders or arrhythmias: bradycardia and tachyarrhythmia. Bradycardia occurs when the heart beats too slowly, and may be treated by a common implantable pacemaker delivering low voltage (about 3 Volts) pacing pulses.

The common implantable pacemaker is usually contained within a hermetically sealed enclosure, in order to protect the operational components of the device from the harsh environment of the body, as well as to protect the body from the device.

The common implantable pacemaker operates in conjunction with one or more electrically conductive leads, adapted to conduct electrical stimulating pulses to sites within the patient's heart, and to communicate sensed signals from those sites back to the implanted device.

Furthermore, the common implantable pacemaker typically has a metal case and a connector block mounted to the metal case that includes receptacles for leads which may be used for electrical stimulation or which may be used for sensing of physiological signals. The battery and the circuitry associated with the common implantable pacemaker are hermetically sealed within the case. Electrical interfaces are employed to connect the leads outside the metal case with the medical device circuitry and the battery inside the metal case.

Electrical interfaces serve the purpose of providing an electrical circuit path extending from the interior of a hermetically sealed metal case to an external point outside the case while maintaining the hermetic seal of the case. A conductive path is provided through the interface by a conductive pin that is electrically insulated from the case itself.

Such interfaces typically include a ferrule that permits attachment of the interface to the case, the conductive pin, and a hermetic glass or ceramic seal that supports the pin within the ferrule and isolates the pin from the metal case.

A common implantable pacemaker can, under some circumstances, be susceptible to electrical interference such that the desired functionality of the pacemaker is impaired. For example, common implantable pacemaker requires protection against electrical interference from electromagnetic interference defibrillation pulses, electrostatic discharge, or other generally large voltages or currents generated by other devices external to the medical device. As noted above, more recently, it has become crucial that cardiac assist systems be protected from magnetic-resonance imaging sources.

Such electrical interference can damage the circuitry of the cardiac assist systems or cause interference in the proper operation or functionality of the cardiac assist systems. For example, damage may occur due to high voltages or excessive currents introduced into the cardiac assist system.

Therefore, it is required that such voltages and currents be limited at the input of such cardiac assist systems, e.g., at the interface. Protection from such voltages and currents has typically been provided at the input of a cardiac assist system by the use of one or more zener diodes and one or more filter capacitors.

For example, one or more zener diodes may be connected between the circuitry to be protected, e.g., pacemaker circuitry, and the metal case of the medical device in a manner which grounds voltage surges and current surges through the diode(s). Such zener diodes and capacitors used for such applications may be in the form of discrete components mounted relative to circuitry at the input of a connector block where various leads are connected to the implantable medical device, e.g., at the interfaces for such leads.

However, such protection, provided by zener diodes and capacitors placed at the input of the medical device, increases the congestion of the medical device circuits, at least one zener diode and one capacitor per input/output connection or interface. This is contrary to the desire for increased miniaturization of implantable medical devices.

Further, when such protection is provided, interconnect wire length for connecting such protection circuitry and pins of the interfaces to the medical device circuitry that performs desired functions for the medical device tends to be undesirably long. The excessive wire length may lead to signal loss and undesirable inductive effects. The wire length can also act as an antenna that conducts undesirable electrical interference signals to sensitive CMOS circuits within the medical device to be protected.

Additionally, the radio-frequency energy that is inductively coupled into the wire causes intense heating along the length of the wire, and at the electrodes that are attached to the heart wall. This heating may be sufficient to ablate the interior surface of the blood vessel through which the wire lead is placed, and may be sufficient to cause scarring at the point where the electrodes contact the heart. A further result of this ablation and scarring is that the sensitive node that the electrode is intended to pace with low voltage signals becomes desensitized, so that pacing the patient's heart becomes less reliable, and in some cases fails altogether.

Another conventional solution for protecting the implantable medical device from electromagnetic interference is illustrated in FIG. 1. FIG. 1 is a schematic view of an implantable medical device 12 embodying protection against electrical interference. At least one lead 14 is connected to the implantable medical device 12 in connector block region 13 using an interface.

In the case where implantable medical device 12 is a pacemaker implanted in a body 10, the pacemaker 12 includes at least one or both of pacing and sensing leads represented generally as leads 14 to sense electrical signals attendant to the depolarization and repolarization of the heart 16, and to provide pacing pulses for causing depolarization of cardiac tissue in the vicinity of the distal ends thereof.

Conventionally protection circuitry is provided using a diode array component. The diode array conventionally consists of five zener diode triggered semiconductor controlled rectifiers with anti-parallel diodes arranged in an array with one common connection. This allows for a small footprint despite the large currents that may be carried through the device during defibrillation, e.g., 10 amps. The semiconductor controlled rectifiers turn ON and limit the voltage across the device when excessive voltage and current surges occur.

Each of the zener diode triggered semiconductor controlled rectifier is connected to an electrically conductive pin. Further, each electrically conductive pin is connected to a medical device contact region to be wire bonded to pads of a printed circuit board. The diode array component is connected to the electrically conductive pins via the die contact regions along with other electrical conductive traces of the printed circuit board.

Other attempts have been made to protect implantable devices from magnetic-resonance imaging fields. For example, U.S. Pat. No. 5,968,083 describes a device adapted to switch between low and high impedance modes of operation in response to electromagnetic interference or insult.

Furthermore, U.S. Pat. No. 6,188,926 discloses a control unit for adjusting a cardiac pacing rate of a pacing unit to an interference backup rate when heart activity cannot be sensed due to electromagnetic interference or insult.

Although, conventional medical devices provide some means for protection against electromagnetic interference, these conventional devices require much circuitry and fail to provide fail-safe protection against radiation produced by magnetic-resonance imaging procedures. Moreover, the conventional devices fail to address the possible damage that can be done at the tissue interface due to radio-frequency induced heating, and they fail to address the unwanted heart stimulation that may result from radio-frequency induced electrical currents.

Thus, it is desirable to provide devices that prevent the possible damage that can be done at the tissue interface due to induced electrical signals that may cause thermally-related tissue damage.

SUMMARY OF THE PRESENT INVENTION

One aspect of the present invention is a lead. The lead includes a conductor having a distal end and a proximal end and a resonant circuit operatively connected to the conductor, the resonant circuit having a resonance frequency approximately equal to an excitation signal's frequency of a magnetic-resonance imaging scanner.

A second aspect of the present invention is a bipolar pacing lead circuit. The bipolar pacing lead circuit includes first and second conductors, the first and second conductors each having a distal end and a proximal end, and a resonant circuit operatively connected to the first conductor. The resonant circuit has a resonance frequency approximately equal to an excitation signal's frequency of a magnetic-resonance imaging scanner.

Another aspect of the present invention is an adapter for a lead. The adapter includes a housing having a first connector and a second connector, the first connector providing a mechanical and electrical connection to a lead, the second connector providing a mechanical and electrical connection to a medical device, and a resonant circuit operatively connected to the first and second connectors. The resonant circuit has a resonance frequency approximately equal to an excitation signal's frequency of a magnetic-resonance imaging scanner.

Another aspect of the present invention is an adapter for a bipolar pacing lead. The adapter includes a housing having a first connector and a second connector, the first connector providing a mechanical and electrical connection to each lead of a multi-conductor lead, the second connector providing a mechanical and electrical connection to a medical device, and a resonant circuit operatively connected to the first and second connectors. The resonant circuit has a resonance frequency approximately equal to an excitation signal's frequency of a magnetic-resonance imaging scanner.

Another aspect of the present invention is an adapter for a lead. The adapter includes a housing having a first connector said first connector providing a mechanical and electrical connection to a lead; a resonant circuit operatively connected to the first connector; and a medical device operatively connected to the resonant circuit. The resonant circuit has a resonance frequency approximately equal to an excitation signal's frequency of a magnetic-resonance imaging scanner.

Another aspect of the present invention is a medical device. The medical device includes a housing having electronic components therein; a lead operatively connected to the electronic components within the housing; and a resonant circuit, located within the housing, operatively connected to the lead and the electronic components. The resonant circuit has a resonance frequency approximately equal to an excitation signal's frequency of a magnetic-resonance imaging scanner.

Another aspect of the present invention is a medical device. The medical device includes a housing having electronic components therein; a multi-conductor lead circuit operatively connected to the electronic components within the housing; and a resonant circuit, located within the housing, operatively connected to a conductor of the multi-conductor lead circuit and the electronic components. The resonant circuit has a resonance frequency approximately equal to an excitation signal's frequency of a magnetic-resonance imaging scanner.

Another aspect of the present invention is a lead. The lead includes a conductor having a distal end and a proximal end and a resonant circuit operatively connected to the conductor. The resonant circuit has a resonance frequency approximately equal to a frequency of an electromagnetic radiation source.

Another aspect of the present invention is a medical device. The medical device includes a housing having electronic components therein; a lead operatively connected to the electronic components within the housing; and a resonant circuit, located within the housing, operatively connected to the lead and the electronic components. The resonant circuit has a resonance frequency approximately equal to a frequency of an electromagnetic radiation source.

Another aspect of the present invention is a medical device. The medical device includes a housing having electronic components therein; a multi-conductor lead operatively connected to the electronic components within the housing; and a resonant circuit, located within the housing, operatively connected to the multi-conductor lead and the electronic components. The resonant circuit has a resonance frequency approximately equal to a frequency of an electromagnetic radiation source.

Another aspect of the present invention is an adapter for a lead. The adapter includes a housing having a first connector and a second connector, the first connector providing a mechanical and electrical connection to a lead, the second connector providing a mechanical and electrical connection to a medical device; and a resonant circuit operatively connected to the first and second connectors. The resonant circuit has a resonance frequency approximately equal to a frequency of an electromagnetic radiation source.

Another aspect of the present invention is an adapter for a lead. The adapter includes a housing having a first connector and a second connector, the first connector providing a mechanical and electrical connection to each lead of a multi-conductor lead, the second connector providing a mechanical and electrical connection to a medical device; and a resonant circuit operatively connected to the first and second connectors. The resonant circuit has a resonance frequency approximately equal to a frequency of an electromagnetic radiation source.

Another aspect of the present invention is an adapter for a lead. The adapter includes a housing having a first connector the first connector providing a mechanical and electrical connection to a lead; a resonant circuit operatively connected to the first connector; and a medical device operatively connected to the resonant circuit. The resonant circuit has a resonance frequency approximately equal to a frequency of an electromagnetic radiation source.

Another aspect of the present invention is a lead. The lead includes a conductor having a distal end and a proximal end and a resonant circuit operatively connected to the conductor, the resonant circuit having a resonance frequency not tuned to an excitation signal's frequency of a magnetic-resonance imaging scanner.

Another aspect of the present invention is a bipolar pacing lead circuit. The bipolar pacing lead circuit includes first and second conductors, the first and second conductors each having a distal end and a proximal end, and a resonant circuit operatively connected to the first conductor. The resonant circuit has a resonance frequency not tuned to an excitation signal's frequency of a magnetic-resonance imaging scanner.

Another aspect of the present invention is an adapter for a lead. The adapter includes a housing having a first connector and a second connector, the first connector providing a mechanical and electrical connection to a lead, the second connector providing a mechanical and electrical connection to a medical device, and a resonant circuit operatively connected to the first and second connectors. The resonant circuit has a resonance frequency not tuned to an excitation signal's frequency of a magnetic-resonance imaging scanner.

Another aspect of the present invention is an adapter for a bipolar pacing lead. The adapter includes a housing having a first connector and a second connector, the first connector providing a mechanical and electrical connection to each lead of a multi-conductor lead, the second connector providing a mechanical and electrical connection to a medical device, and a resonant circuit operatively connected to the first and second connectors. The resonant circuit has a resonance frequency not tuned to an excitation signal's frequency of a magnetic-resonance imaging scanner.

Another aspect of the present invention is a medical device. The medical device includes a housing having electronic components therein; a lead operatively connected to the electronic components within the housing; and a resonant circuit, located within the housing, operatively connected to the lead and the electronic components. The resonant circuit has a resonance frequency not tuned to an excitation signal's frequency of a magnetic-resonance imaging scanner.

Another aspect of the present invention is a medical device. The medical device includes a housing having electronic components therein; a multi-conductor lead circuit operatively connected to the electronic components within the housing; and a resonant circuit, located within the housing, operatively connected to a conductor of the multi-conductor lead circuit and the electronic components. The resonant circuit has a resonance frequency not tuned to an excitation signal's frequency of a magnetic-resonance imaging scanner.

Another aspect of the present invention is a lead. The lead includes a conductor having a distal end and a proximal end and a resonant circuit operatively connected to the conductor. The resonant circuit has a resonance frequency not tuned to a frequency of an electromagnetic radiation source.

Another aspect of the present invention is a medical device. The medical device includes a housing having electronic components therein; a lead operatively connected to the electronic components within the housing; and a resonant circuit, located within the housing, operatively connected to the lead and the electronic components. The resonant circuit has a resonance frequency not tuned to a frequency of an electromagnetic radiation source.

Another aspect of the present invention is a medical device. The medical device includes a housing having electronic components therein; a multi-conductor lead operatively connected to the electronic components within the housing; and a resonant circuit, located within the housing, operatively connected to the multi-conductor lead and the electronic components. The resonant circuit has a resonance frequency not tuned to a frequency of an electromagnetic radiation source.

Another aspect of the present invention is an adapter for a lead. The adapter includes a housing having a first connector and a second connector, the first connector providing a mechanical and electrical connection to a lead, the second connector providing a mechanical and electrical connection to a medical device; and a resonant circuit operatively connected to the first and second connectors. The resonant circuit has a resonance frequency not tuned to a frequency of an electromagnetic radiation source.

Another aspect of the present invention is an adapter for a lead. The adapter includes a housing having a first connector and a second connector, the first connector providing a mechanical and electrical connection to each lead of a multi-conductor lead, the second connector providing a mechanical and electrical connection to a medical device; and a resonant circuit operatively connected to the first and second connectors. The resonant circuit has a resonance frequency not tuned to a frequency of an electromagnetic radiation source.

Another aspect of the present invention is an adapter for a lead. The adapter includes a housing having a first connector the first connector providing a mechanical and electrical connection to a lead; a resonant circuit operatively connected to the first connector; and a medical device operatively connected to the resonant circuit. The resonant circuit has a resonance frequency not tuned to a frequency of an electromagnetic radiation source.

Another aspect of the present invention is an adapter for a lead. The adapter includes a housing having a first connector said first connector providing a mechanical and electrical connection to a lead; a resonant circuit operatively connected to the first connector; and a medical device operatively connected to the resonant circuit. The resonant circuit has a resonance frequency not tuned to an excitation signal's frequency of a magnetic-resonance imaging scanner.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

As noted above, a medical device includes an anti-antenna device to prevent or significantly reduce damaging heat, created by currents or voltages induced by outside electromagnetic energy (namely magnetic-resonance imaging), to a tissue area.

More specifically, the present invention is directed to a medical device that includes anti-antenna device, which significantly reduces the induced current on the "signal" wire of a pacing lead when the pacing lead is subjected to the excitation signal's frequency of a magnetic-resonance imaging scanner without significantly altering a low frequency pacing signal. The low frequency pacing signal may be generated by an implantable pulse generator or other pulse generator source outside the body.

To provide an anti-antenna device, the present invention utilizes a resonant circuit or circuits in line with a lead. The lead may be a signal wire of the pacing lead. Although the following descriptions of the various embodiments of the present invention, as well as the attached claims may utilize, the term pacing lead or lead, the term pacing lead or lead may generically refer to a unipolar pacing lead having one conductor; a bipolar pacing lead having two conductors; an implantable cardiac defibrillator lead; a deep brain stimulating lead having multiple conductors; a nerve stimulating lead; and/or any other medical lead used to deliver an electrical signal to or from a tissue area of a body. The resonant circuit or circuits provide a blocking quality with respect to the currents induced by the excitation signal's frequency of the magnetic-resonance imaging scanner. The excitation signal's frequency of the magnetic-resonance imaging scanner is commonly defined as the rotational frequency of the scanner's excitation magnetic field, commonly known as the scanner's B1 field.

Figure 1:
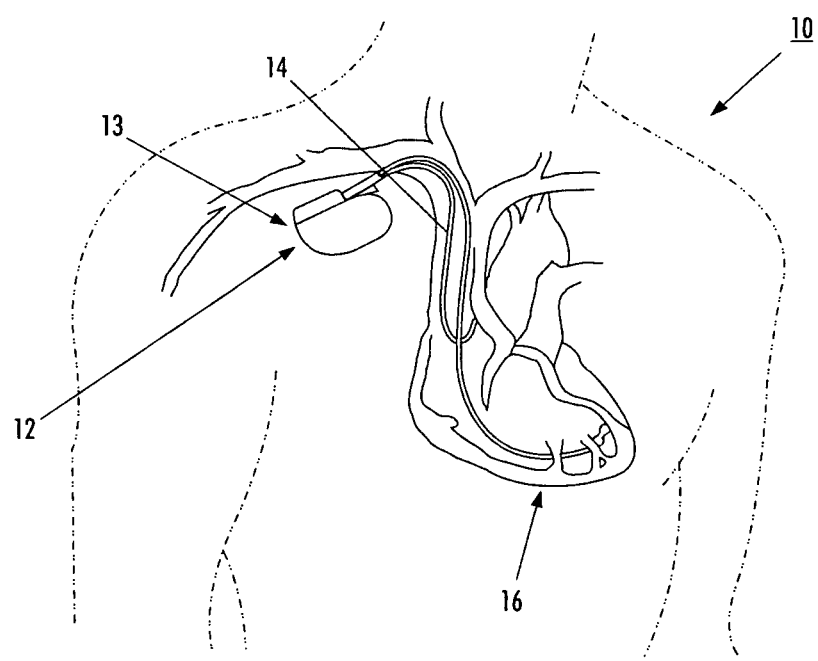
FIG. 1 is an illustration of conventional cardiac assist device.
Figure 2:
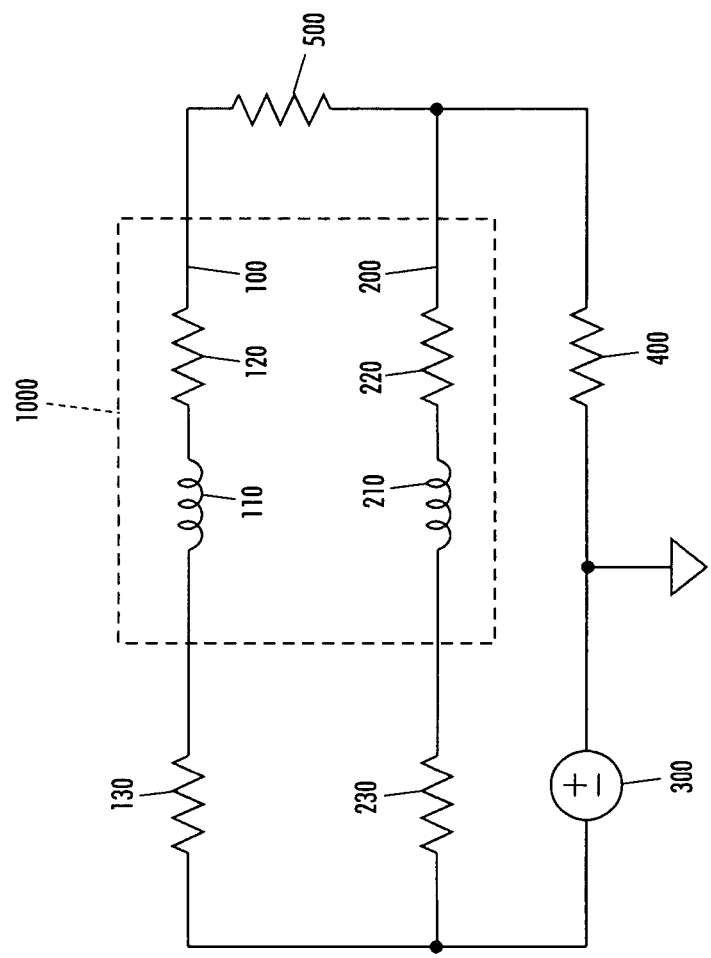
FIG. 2 shows a conventional bipolar pacing lead circuit representation.

FIG. 2 provides a conventional circuit representation of a bipolar pacing lead. As illustrated in FIG. 2, the bipolar pacing lead 1000 includes two leads (100 and 200). A first pacing lead 100 includes resistance and inductance represented by a first resistor 120 and a first inductor 110, respectively. A second pacing lead 200 includes resistance and inductance represented by a second resistor 220 and a second inductor 210, respectively. At a distal end of each lead, the leads (100 and 200) come in contact with tissue.

As illustrated in FIG. 2, the circuit paths from the distal ends of the leads (100 and 200) include a first tissue resistance, represented by first tissue modeled resistor 130, and a second tissue resistance, represented by second tissue modeled resistor 230.

The conventional circuit representation of a bipolar pacing lead, as illustrated in FIG. 2, further includes a voltage source 300 that represents the induced electromagnetic energy (voltage or current) from magnetic resonance imaging, a body modeled resistor 400 that represents the resistance of the body, and a differential resistor 500 that represents a resistance between the leads.

Figure 3:
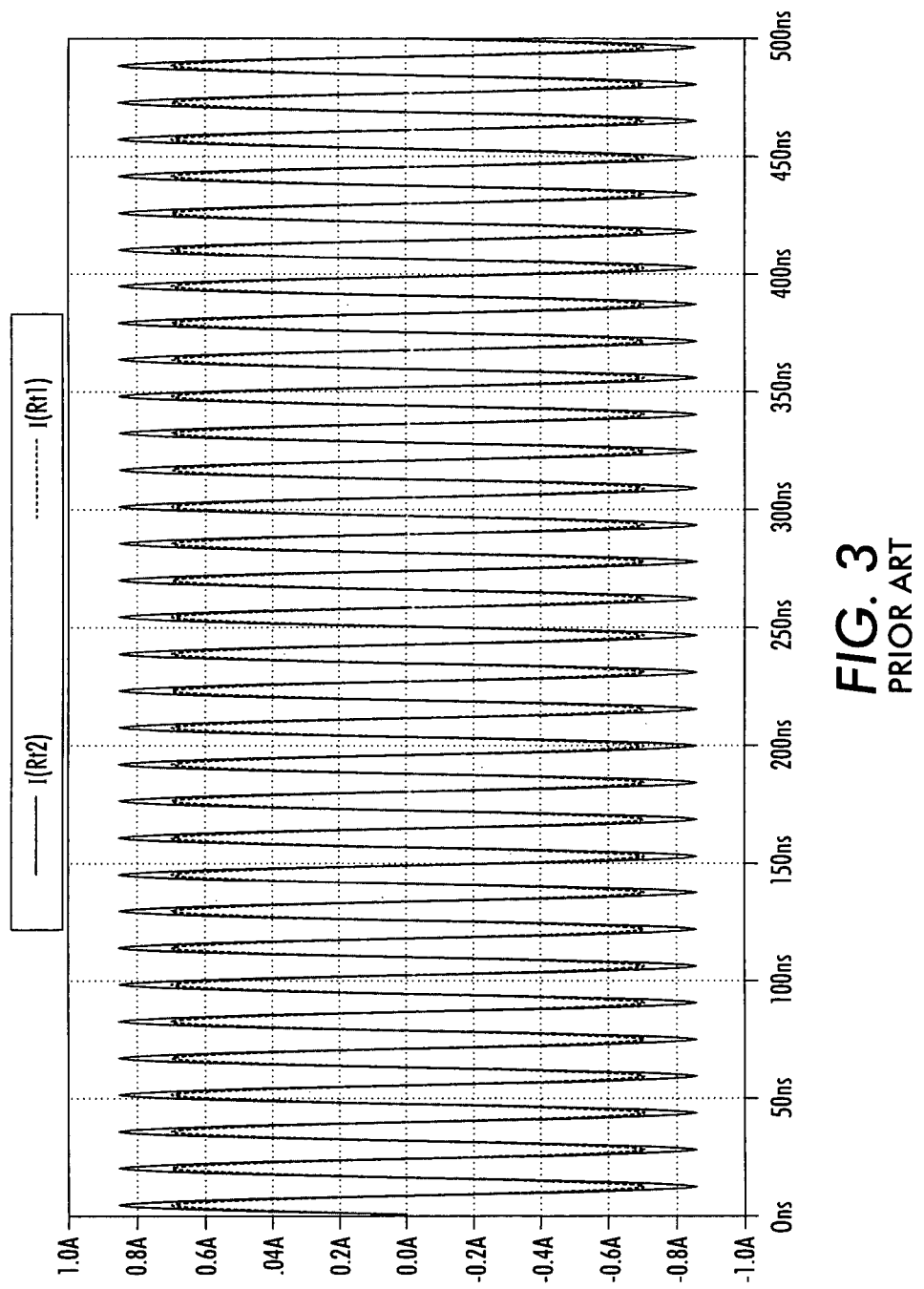
FIG. 3 is a graph illustrating the magnitude of the current, induced by magnetic-resonance imaging, flowing through the tissue at a distal end of a medical device using the bipolar pacing lead circuit of FIG. 2.

In FIG. 3, it is assumed that the bipolar pacing leads of FIG. 2 are subjected to a 64 MHz magnetic resonance imaging environment. As demonstrated in FIG. 3, the current induced by the 64 MHz magnetic resonance imaging environment and flowing through the tissue at the distal end of the bipolar pacing leads can have a magnitude between 0.85 and −0.85 amps. This magnitude of current (IRt2, which represents the current flowing through first tissue modeled resistors 130 and IRt1, which represents the current flowing through second tissue modeled resistors 230) at the distal end of the bipolar pacing leads can lead to serious damage to the tissue due to heat generated by the current flowing to the tissue.

Figure 4:
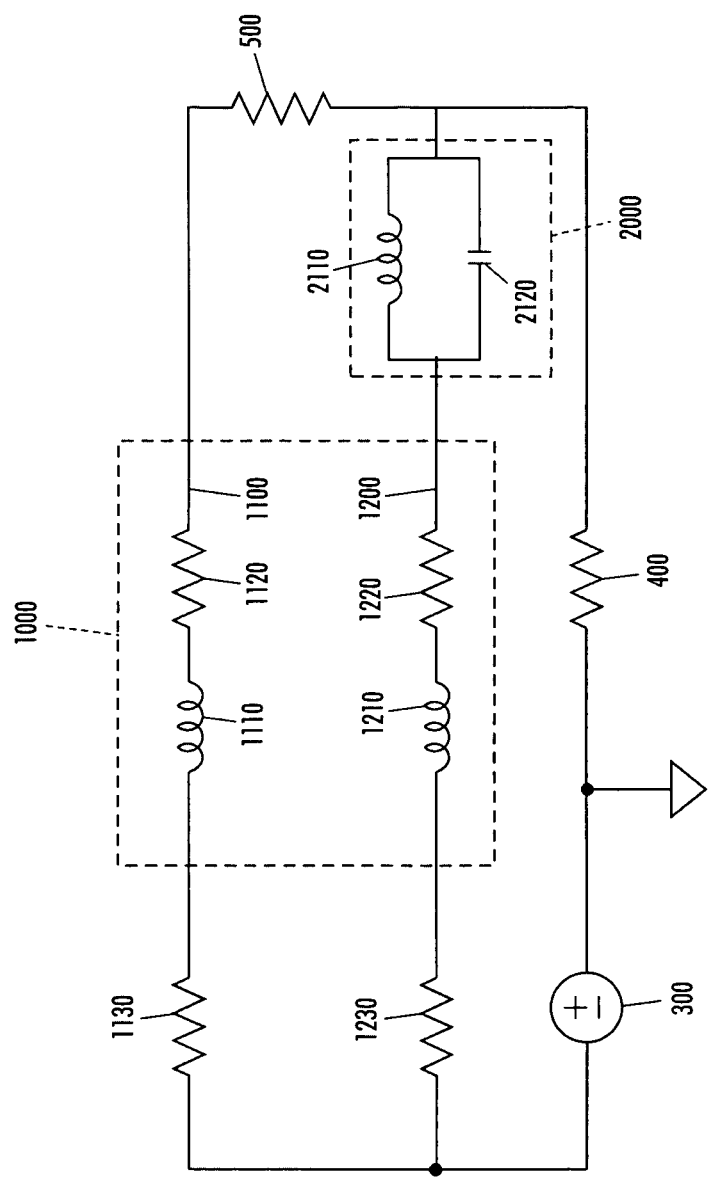
FIG. 4 shows a bipolar pacing lead circuit representation according to some or all of the concepts of the present invention.

To reduce the heat generated by the induced current in the tissue, FIG. 4 provides a circuit representation of a bipolar pacing lead according to the concepts of the present invention. As illustrated in FIG. 4, the bipolar pacing lead 1000 includes two leads (1100 and 1200); A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 4, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 4, further includes a voltage source 300 that represents the induced electromagnetic energy (voltage or current) from magnetic resonance imaging, a body modeled resistor 400 that represents the resistance of the body, and a differential resistor 500 that represents a resistance between the leads.

In addition to the elements discussed above, the circuit representation of a bipolar pacing lead, as illustrated in FIG. 4, includes a resonant circuit 2000 in series or inline with one of the pacing leads, namely the second lead 1200. The resonant circuit 2000 includes a LC circuit having an inductor 2110 in parallel to a capacitor 2120. The resonant circuit 2000 acts as an anti-antenna device, thereby reducing the magnitude of the current induced through the tissue at the distal end of the pacing leads (1100 and 1200).

Figure 5:
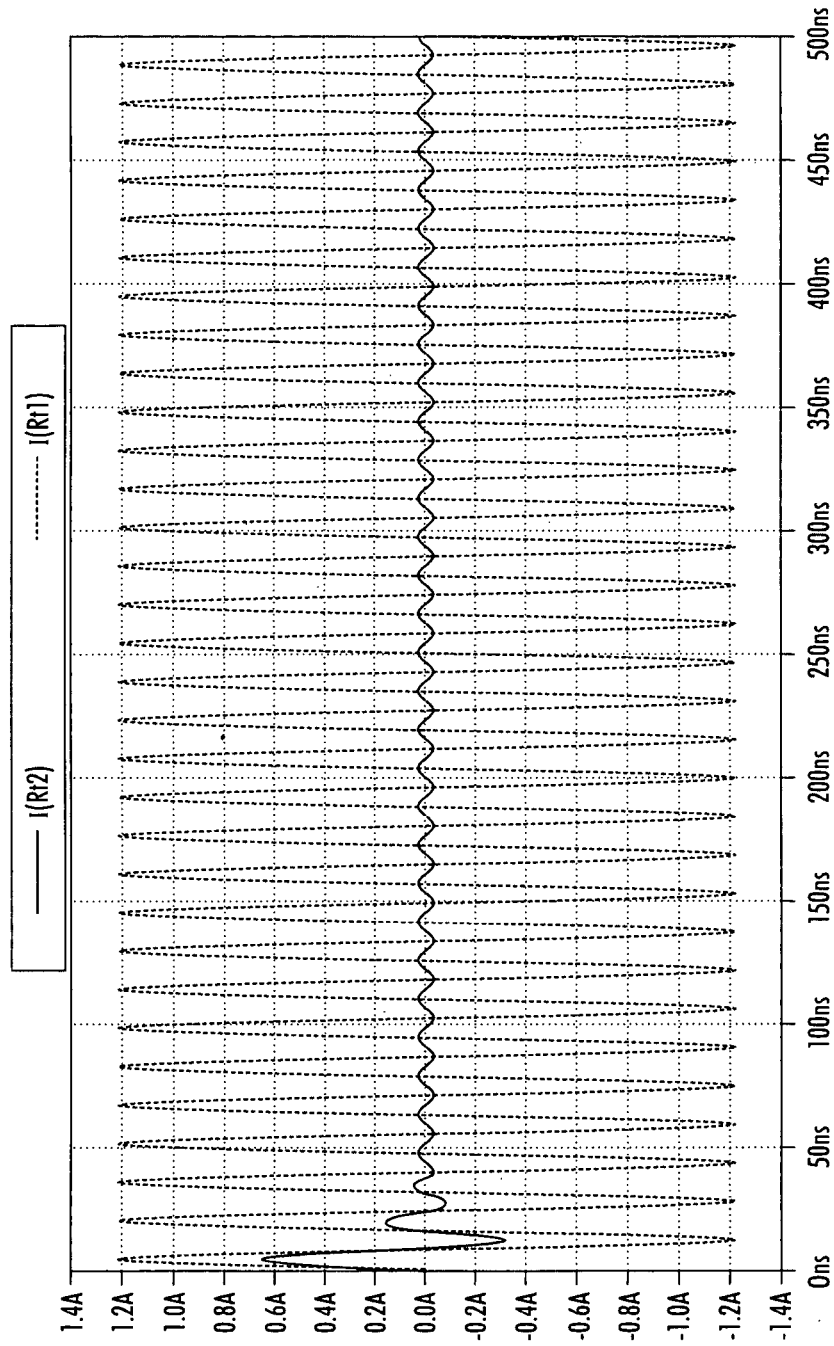
FIG. 5 is a graph illustrating the magnitude of the current, induced by magnetic-resonance imaging, flowing through the tissue at a distal end of a medical device using the bipolar pacing lead circuit of FIG. 4.

In FIG. 5, it is assumed that the bipolar pacing leads of FIG. 4 are subjected to a 64 MHz magnetic resonance imaging environment. As demonstrated in FIG. 5, the current (IRt2, which represents the current flowing through tissue modeled resistor 1230 of FIG. 4) induced by the 64 MHz magnetic resonance imaging environment and flowing through the tissue at the distal end of the second bipolar pacing lead 1200 can be greatly reduced. It is noted that the current (IRt1, which represents the current flowing through tissue modeled resistor 1130 of FIG. 4) induced by the 64 MHz magnetic resonance imaging environment and flowing through the tissue at the distal end of the second bipolar pacing lead 1100 can have a magnitude between 1.21 and −1.21 amps. This reduced magnitude of current (IRt2, which represents the current flowing through tissue modeled resistor 1230 of FIG. 4) at the distal end of the bipolar pacing lead can significantly reduce the damage to the tissue due to heat generated by the current flowing to the tissue.

Figure 6:
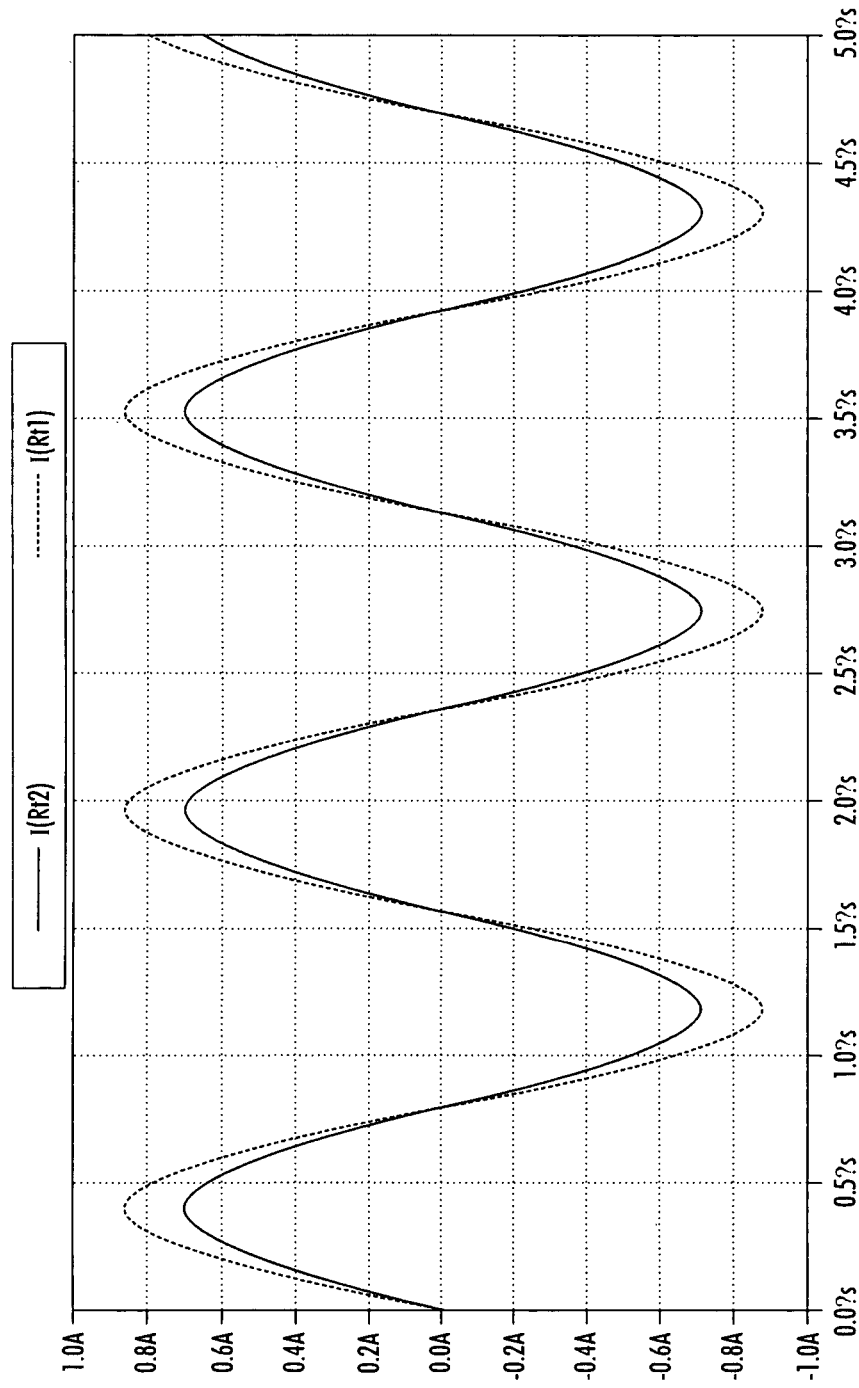
FIG. 6 is a graph illustrating the magnitude of the current, low-frequency pacing or defibrillation signals, flowing through the circuit of a medical device using the bipolar pacing lead circuit of FIG. 4.

Notwithstanding the inclusion of the resonant circuit 2000, the bipolar pacing leads can still provide an efficient pathway for the pacing signals, as illustrated by FIG. 6. As can be seen when compared to FIG. 3, the current magnitudes shown in FIG. 6 through tissue resistors 1130 and 1230, shown in FIG. 4, are approximately the same as the magnitudes of the currents passing through tissue resistors 130 and 230, shown in FIG. 2. Thus, with the resonant circuit 2000 inserted into the circuit of FIG. 4, the low frequency pacing signals are not significantly altered.

Figure 7:
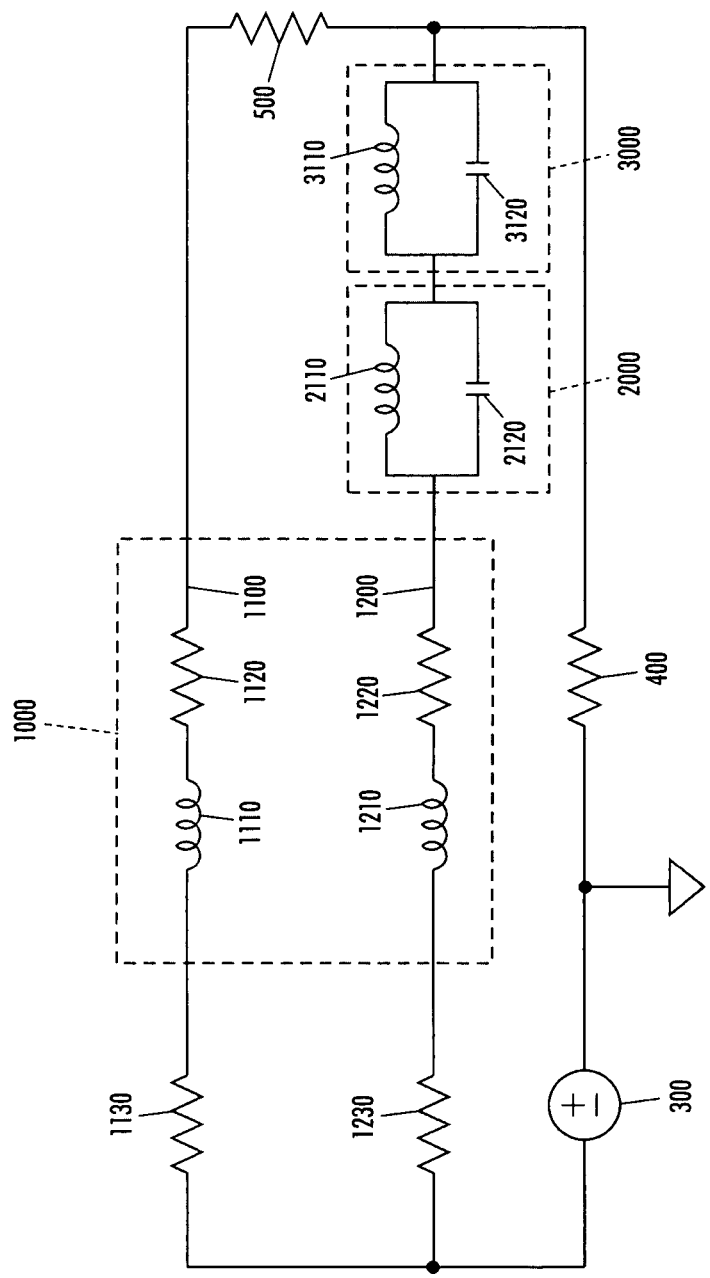
FIG. 7 shows another bipolar pacing lead circuit representation according to some or all of the concepts of the present invention.

To provide a further reduction of the heat generated by the induced current in the tissue, FIG. 7 provides a circuit representation of a bipolar pacing lead according to the concepts of the present invention. As illustrated in FIG. 7, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 7, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 7, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 7, includes two resonant circuits (2000 and 3000) in series or inline with one of the pacing leads, namely the second lead 1200. The first resonant circuit 2000 includes a LC circuit, tuned to about 64 MHz, having an inductor 2110 in parallel to a capacitor 2120. The second resonant circuit 3000 includes a LC circuit, tuned to about 128 MHz, having an inductor 3110 in parallel to a capacitor 3120.

The resonant circuits (2000 and 3000) act as an anti-antenna device, thereby reducing the magnitude of the current induced through the tissue at the distal end of the pacing lead (1200).

Figure 8:
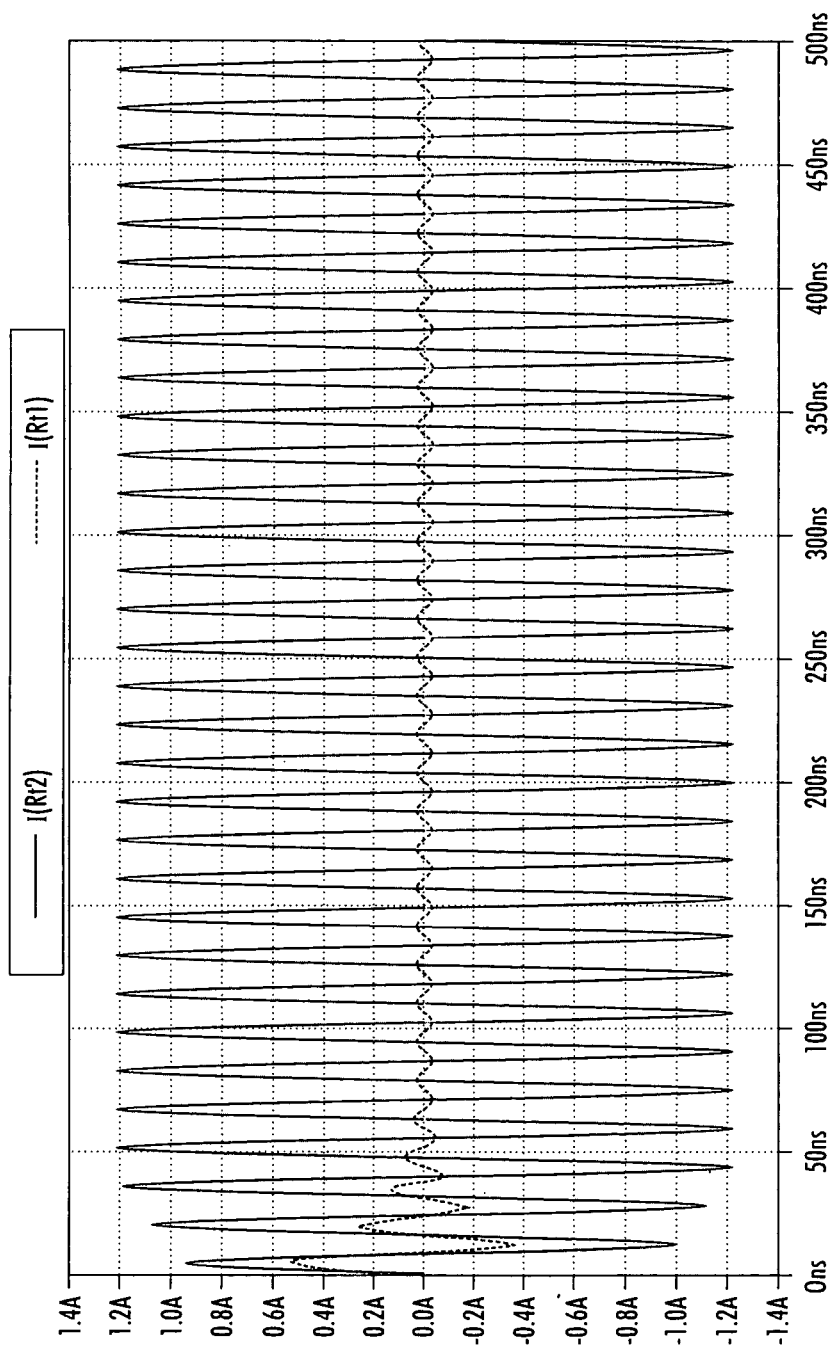
FIG. 8 is a graph illustrating the magnitude of the current, induced by 64 MHz magnetic-resonance imaging, flowing through the tissue at a distal end of a medical device using the bipolar pacing lead circuit of FIG. 7.

In FIG. 8, it is assumed that the bipolar pacing leads of FIG. 7 are subjected to a 64 MHz magnetic resonance imaging environment. As demonstrated in FIG. 8, the current (IRt1, which represents the current flowing through tissue modeled resistor 1230 of FIG. 7) induced by the 64 MHz magnetic resonance imaging environment and flowing through the tissue at the distal end of the second bipolar pacing lead 1200 can be greatly reduced. It is noted that the current (IRt2, which represents the current flowing through tissue modeled resistor 1130 of FIG. 7) induced by the 64 MHz magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 7) at the distal end of the bipolar pacing lead can significantly reduce the damage to the tissue due to heat generated by the current flowing to the tissue.

Figure 9:
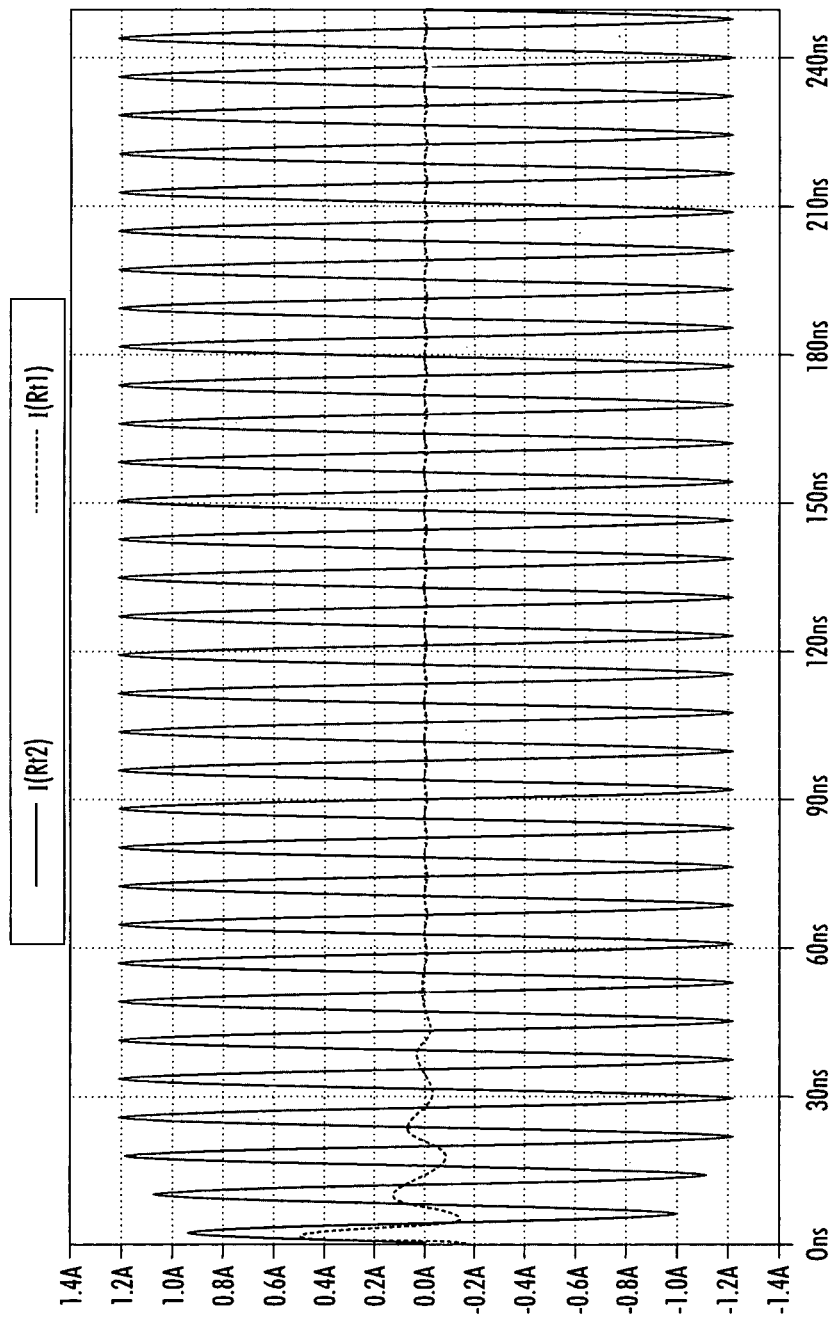
FIG. 9 is a graph illustrating the magnitude of the current, induced by 128 MHz magnetic-resonance imaging, flowing through the tissue at a distal end of a medical device using the bipolar pacing lead circuit of FIG. 7.

In FIG. 9, it is assumed that the bipolar pacing leads of FIG. 7 are subjected to a 128 MHz magnetic resonance imaging environment. As demonstrated in FIG. 9, the current (IRt1, which represents the current flowing through tissue modeled resistor 1230 of FIG. 7) induced by the 128 MHz magnetic resonance imaging environment and flowing through the tissue at the distal end of the second bipolar pacing lead 1200 can be greatly reduced. It is noted that the current (IRt2, which represents the current flowing through tissue modeled resistor 1130 of FIG. 7) induced by the 128 MHz magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 7) at the distal end of the bipolar pacing lead can significantly reduce the damage to the tissue due to heat generated by the current flowing to the tissue.

It is noted that by including the two resonant circuits (2000 and 3000), the bipolar pacing leads can reduce heat generation, notwithstanding the operational frequency of the magnetic resonance imaging scanner. It is noted that further resonant circuits may be added, each tuned to a particular operational frequency of a magnetic resonance imaging scanner.

Figure 10:
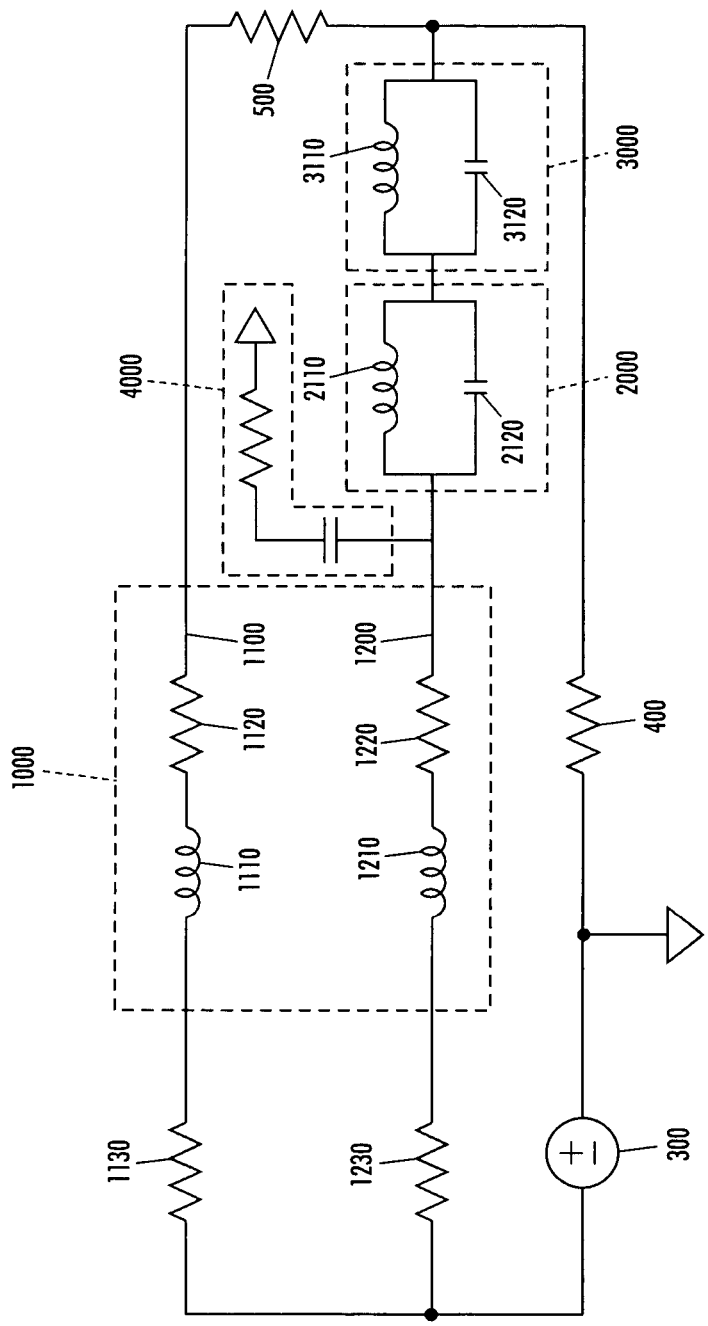
FIG. 10 shows another bipolar pacing lead circuit representation according to some or all of the concepts of the present invention.

To reduction of the heat generated by the induced current in the tissue, FIG. 10 provides a circuit representation of a bipolar pacing lead according to the concepts of the present invention. As illustrated in FIG. 10, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 10, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 10, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 10, includes two resonant circuits (2000 and 3000) in series or inline with one of the pacing leads, namely the second lead 1200. The first resonant circuit 2000 includes a LC circuit, tuned to about 64 MHz, having an inductor 2110 in parallel to a capacitor 2120. The second resonant circuit 3000 includes a LC circuit, tuned to about 128 MHz, having an inductor 3110 in parallel to a capacitor 3120.

The resonant circuits (2000 and 3000) act as an anti-antenna device, thereby reducing the magnitude of the current induced through the tissue at the distal end of the pacing lead (1200).

Lastly, the circuit representation of a bipolar pacing lead, as illustrated in FIG. 10, includes a capacitance circuit 4000 (a capacitor and resistor), which may represent parasitic capacitance or distributive capacitance in the second pacing lead (1200) or additional capacitance added to the pacing lead. It is noted that the parasitic capacitance or distributive capacitance is the inherent capacitance in a pacing lead along its length. Moreover, it is noted that the parasitic capacitance or distributive capacitance may be the inter-loop capacitance in a coiled wire pacing lead. The location of the capacitance circuit 4000 positions the resonant circuits (2000 and 3000) at the proximal end of the pacing lead (1200).

Figure 11:
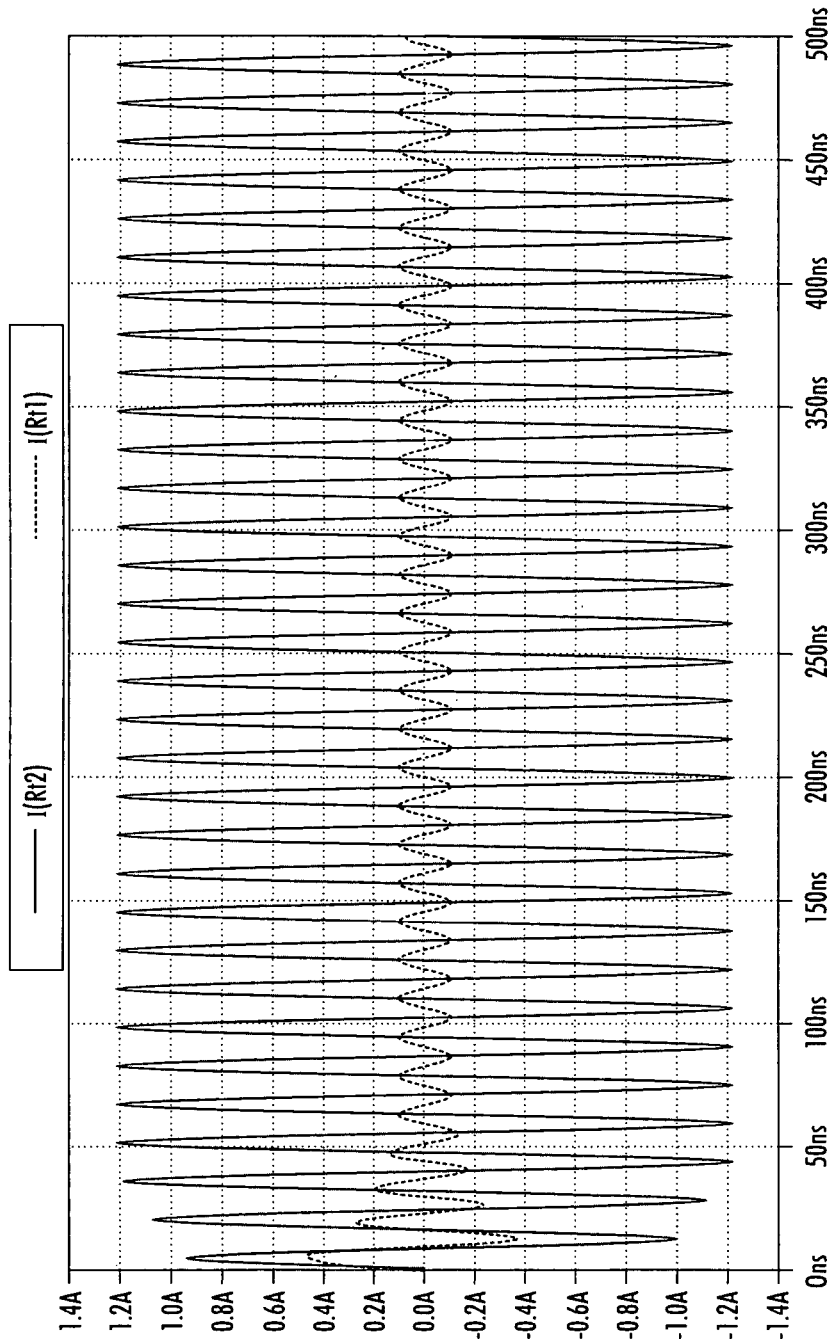
FIG. 11 is a graph illustrating the magnitude of the current, induced by magnetic-resonance imaging, flowing through the tissue at a distal end of a medical device using the bipolar pacing lead circuit of FIG. 10.

In FIG. 11, it is assumed that the bipolar pacing leads of FIG. 10 are subjected to a magnetic resonance imaging environment having an operating radio frequency of approximately 64 MHz. As demonstrated in FIG. 11, the current (IRt1, which represents the current flowing through tissue modeled resistor 1230 of FIG. 10) induced by the magnetic resonance imaging environment and flowing through the tissue at the distal end of the second bipolar pacing lead 1200 is not reduced by the same amount as the previous circuits. In other words, the capacitance circuit 4000 lowers the effectiveness of the resonant circuits (2000 and 3000), located at the proximal end of the lead, to block the magnetic resonance imaging induced currents.

It is noted that the current (IRt2, which represents the current flowing through tissue modeled resistor 1130 of FIG. 10) induced by the magnetic resonance imaging environment and flowing through the tissue at the distal end of the first bipolar pacing lead 1100 can have a magnitude between 1.21 and −1.21 amps.

Although the resonant circuits (2000 and 3000) still reduce the induced current, the capacitance circuit 4000 reduces the effectiveness of the resonant circuits (2000 and 3000). To increase the effectiveness of the resonant circuits (2000 and 3000), the resonant circuits (2000 and 3000) are moved to the distal end of the pacing lead, as illustrated in FIG. 12.

Figure 12:
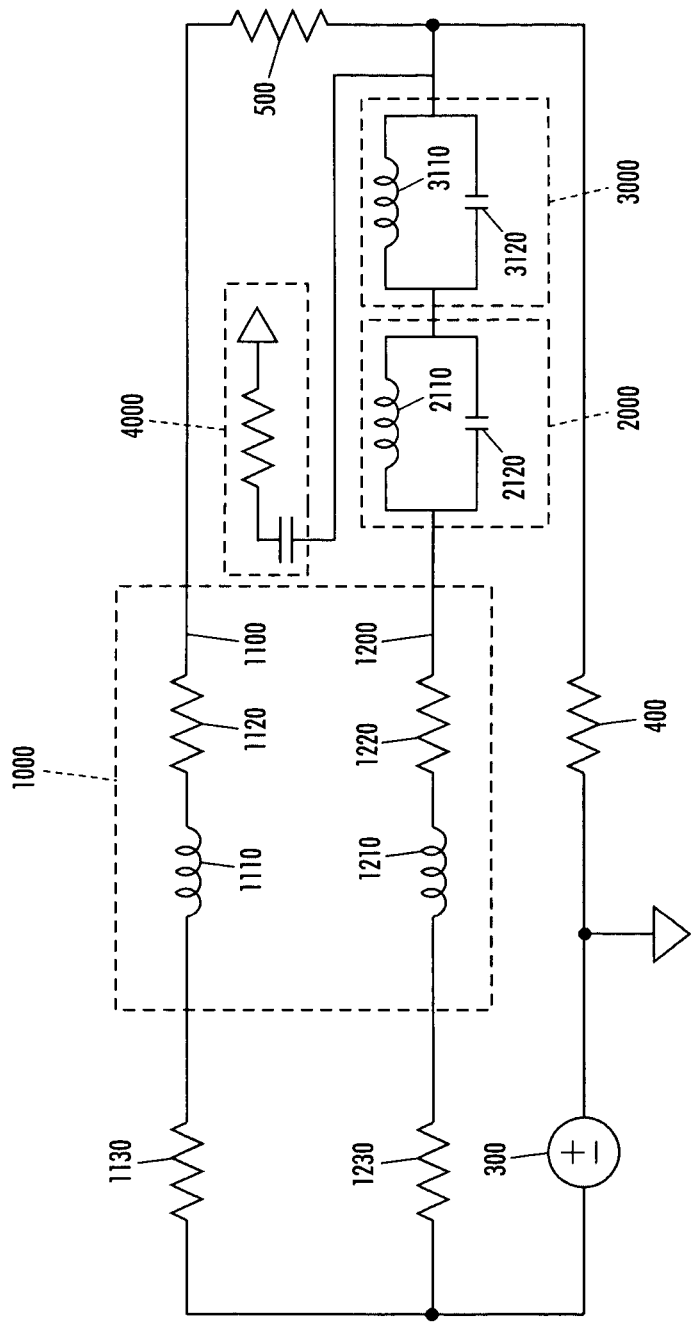
FIG. 12 shows another bipolar pacing lead circuit representation according to some or all of the concepts of the present invention.

To reduction of the heat generated by the induced current in the tissue, FIG. 12 provides a circuit representation of a bipolar pacing lead according to the concepts of the present invention. As illustrated in FIG. 12, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 12, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 12, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 12, includes two resonant circuits (2000 and 3000) in series or inline with one of the pacing leads, namely the second lead 1200. The first resonant circuit 2000 includes a LC circuit, tuned to about 64 MHz, having an inductor 2110 in parallel to a capacitor 2120. The second resonant circuit 3000 includes a LC circuit, tuned to about 128 MHz, having an inductor 3110 in parallel to a capacitor 3120.

The resonant circuits (2000 and 3000) act as an anti-antenna device, thereby reducing the magnitude of the current induced through the tissue at the distal end of the pacing leads (1100 and 1200).

Lastly, the circuit representation of a bipolar pacing lead, as illustrated in FIG. 12, includes a capacitance circuit 4000 (a capacitor and resistor), which may represent parasitic capacitance in the second pacing lead (1200) or additional capacitance added to the pacing lead. The location of the capacitance circuit 4000 positions the resonant circuits (2000 and 3000) at the distal end of the pacing lead (1000).

Figure 13:
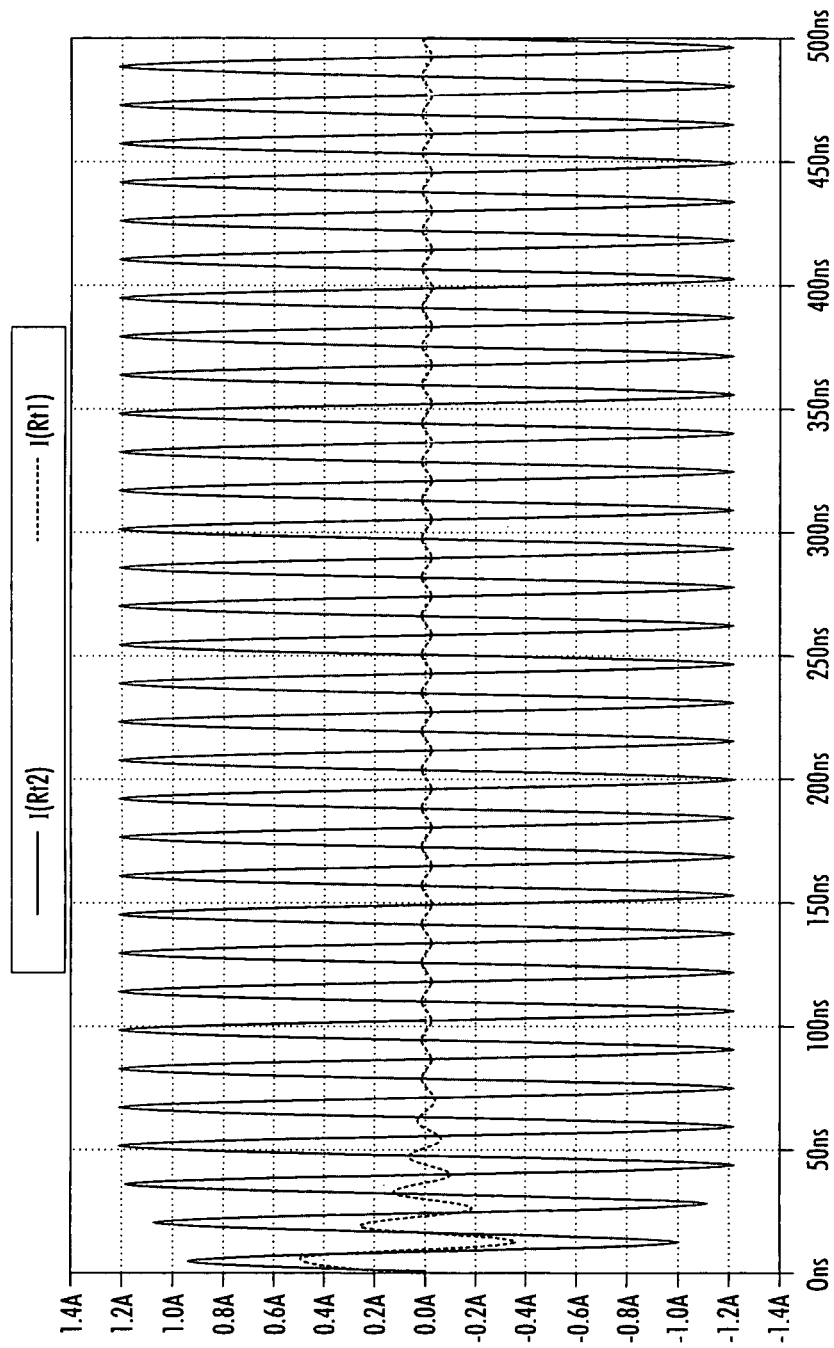
FIG. 13 is a graph illustrating the magnitude of the current, induced by magnetic-resonance imaging, flowing through the tissue at a distal end of a medical device using the bipolar pacing lead circuit of FIG. 12.

In FIG. 13, it is assumed that the bipolar pacing leads of FIG. 12 are subjected to a magnetic resonance imaging environment having an operating radio frequency of approximately 64 MHz. As demonstrated in FIG. 13, the current (IRt1, which represents the current flowing through tissue modeled resistor 1230 of FIG. 12) induced by the magnetic resonance imaging environment and flowing through the tissue at the distal end of the second bipolar pacing lead 1200 is reduced. In other words, the moving of the resonant circuits (2000 and 3000) to the distal end increases the effectiveness of the resonant circuits (2000 and 3000), when a capacitance circuit is involved.

It is noted that the current (IRt2, which represents the current flowing through tissue modeled resistor 1130 of FIG. 12) induced by the magnetic resonance imaging environment and flowing through the tissue at the distal end of the first bipolar pacing lead 1100 can have a magnitude between 1.21 and −1.21 amps.

However, space is very limited at the distal end of the lead. It is noted that the inductor and capacitor values of the resonant circuits (2000 and 3000) can be adjusted which may help reduce the space requirement when implementing the resonant circuit.

The resonance frequency of the circuit is calculated by using the formula $$f_{RES} = \frac{1}{2\pi\sqrt{LC}}$$

The required inductance (L) can be reduced (thereby reducing the physical size required), by increasing the capacitance (C). So, for example, if L=50 nH and C=123.7 pF, and if there is no room in the distal end of the pacing lead for an inductor L having the inductance L=50 nH, an inductor having an inductance of L=25 nH could be used if the capacitor used has a capacitance of 247.4 pF. The resonance frequency remains the same.

Figure 14:
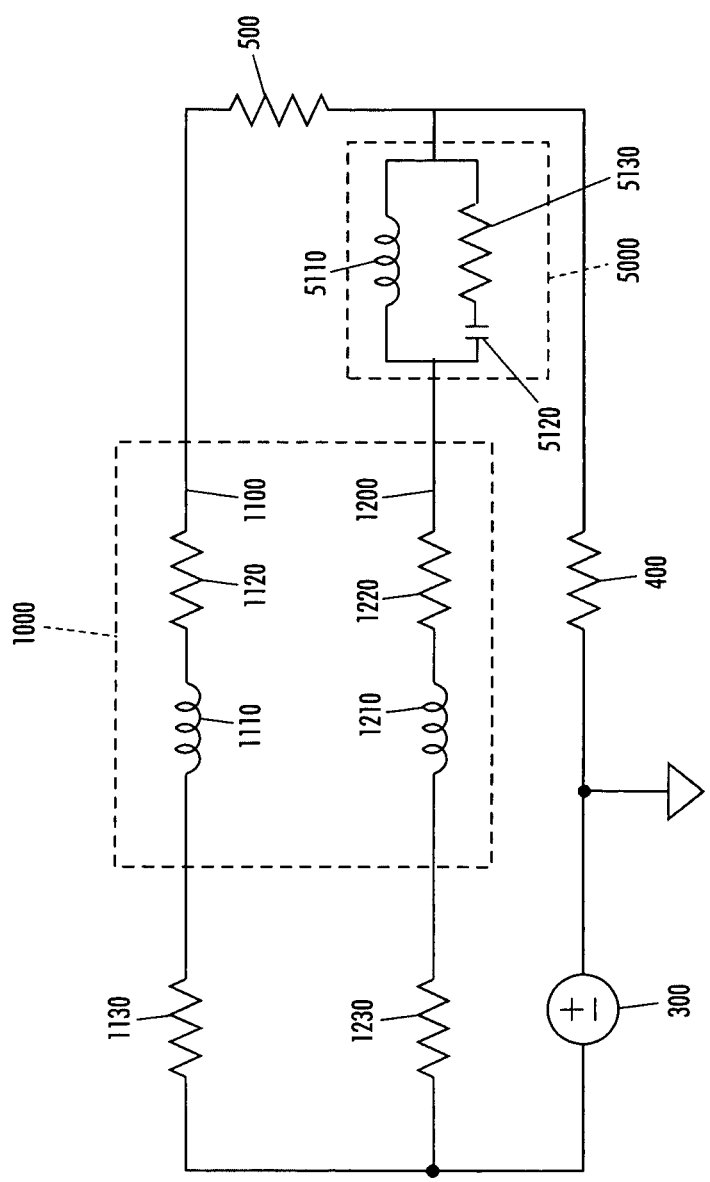
FIG. 14 shows another bipolar pacing lead circuit representation according to some or all of the concepts of the present invention.

To reduction of the heat generated by the induced current in the tissue, FIG. 14 provides a circuit representation of a bipolar pacing lead according to the concepts of the present invention. As illustrated in FIG. 14, the bipolar pacing lead 1000 includes two leads (1100 and 1200). A first pacing lead 1100 includes resistance and inductance represented by a first resistor 1120 and a first inductor 1110, respectively. A second pacing lead 1200 includes resistance and inductance represented by a second resistor 1220 and a second inductor 1210, respectively. At a distal end of each lead, the leads (1100 and 1200) come in contact with tissue.

As illustrated in FIG. 14, the circuit paths from the distal ends of the leads (1100 and 1200) include a first tissue resistance, represented by first tissue modeled resistor 1130, and a second tissue resistance, represented by second tissue modeled resistor 1230.

The circuit representation of a bipolar pacing lead, as illustrated in FIG. 14, further includes a voltage source 300 that represents the induced electromagnetic energy (voltage or current) from magnetic resonance imaging, a body resistor 400 that represents the resistance of the body, and a differential resistor 500 that represents a resistance between the leads.

In addition to the elements discussed above, the circuit representation of a bipolar pacing lead, as illustrated in FIG. 14, includes a resonant circuit (5000) in series or inline with one of the pacing leads, namely the second lead 1200. The resonant circuit 5000 includes a RLC circuit having an inductor 5110 in parallel with a current limiting resistor 5130 and a capacitor 5120.

The resonant circuit (5000) acts as an anti-antenna device, thereby reducing the magnitude of the current induced through the tissue at the distal end of the pacing lead (1200).

The current limiting resistor 5130 reduces the current in the resonant circuit 5000 to make sure that the inductor 5110 is not damaged by too much current passing through it.

Figure 15:
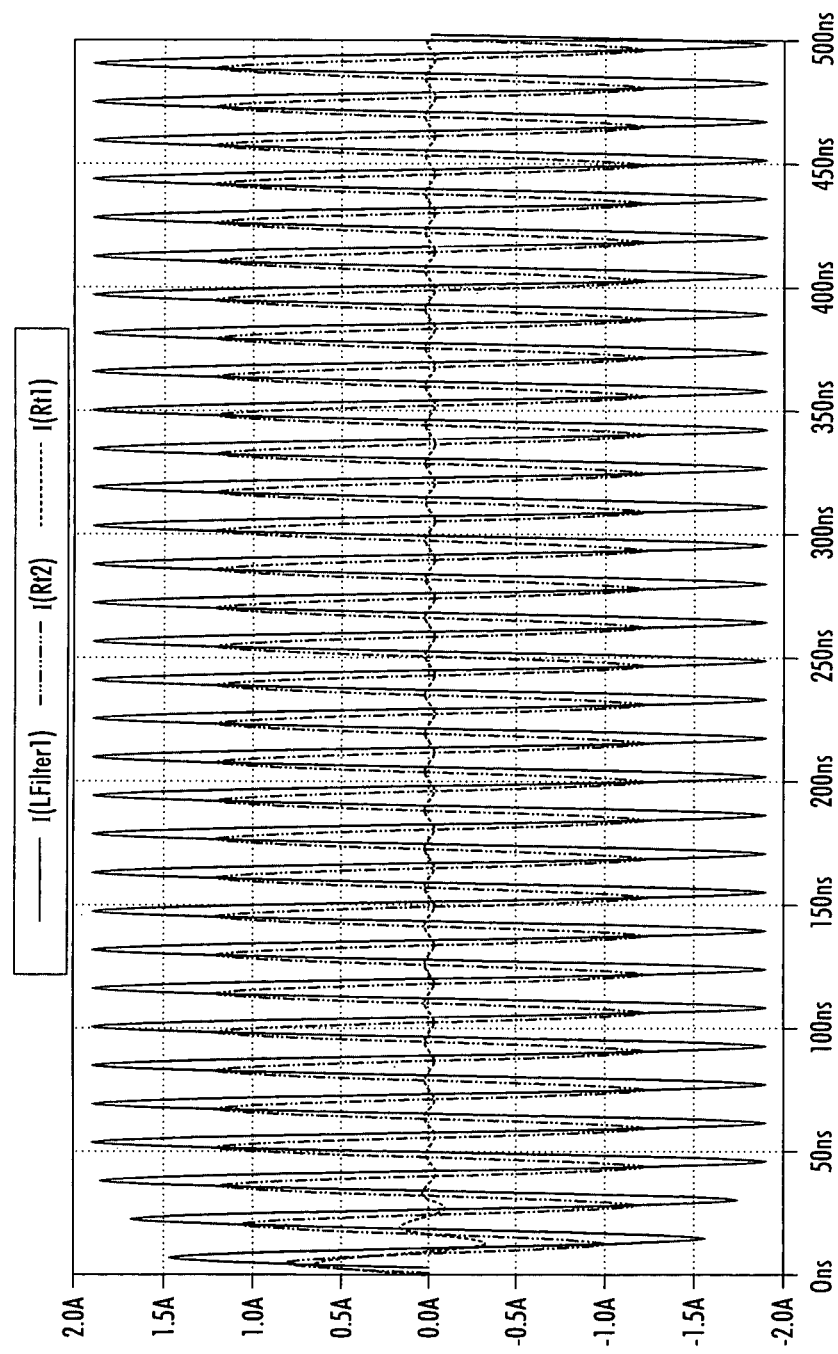
FIG. 15 is a graph illustrating the magnitude of the current, induced by magnetic-resonance imaging, flowing through the tissue at a distal end of a medical device using the bipolar pacing lead circuit of FIG. 14.

FIG. 15, it is assumed that the bipolar pacing leads of FIG. 14 are subjected to a magnetic resonance imaging environment having an operating radio frequency of approximately the resonance frequency of the resonant circuit 5000. As demonstrated in FIG. 15, the current (IRt1, which represents the current flowing through tissue modeled resistor 1230 of FIG. 14) induced by the magnetic resonance imaging environment and flowing through the tissue at the distal end of the second bipolar pacing lead 1200 can be greatly reduced, notwithstanding the addition of the current limiting resistor 5130. It is noted that the current (IRt2, which represents the current flowing through tissue modeled resistor 1130 of FIG. 14) induced by the magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 14) at the distal end of the bipolar pacing lead can significantly reduce the damage to the tissue due to heat generated by the current flowing to the tissue. It is noted that the current ILFilter1 is the current through the inductor 5110 when the resistor 5130 is a small value.

Figure 16:
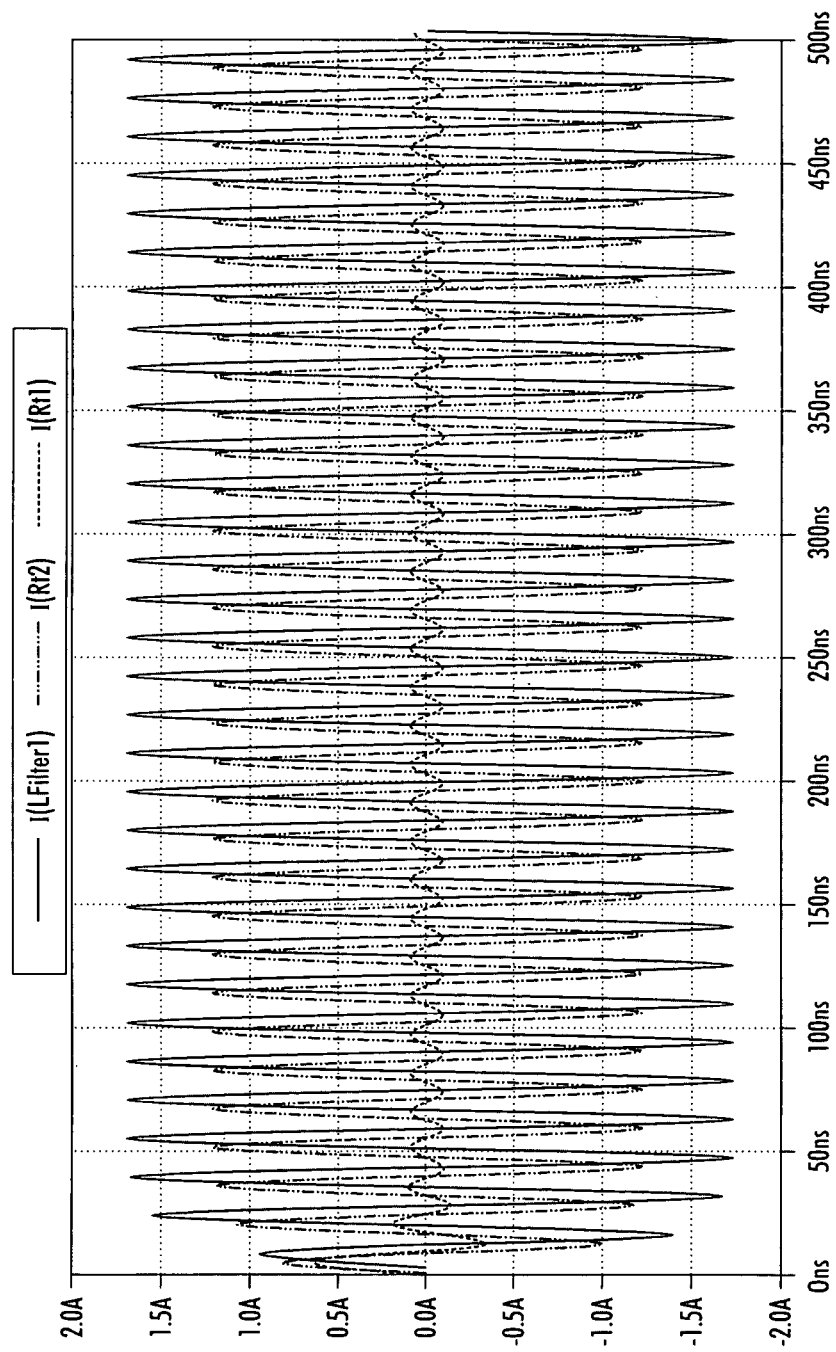
FIG. 16 is a graph illustrating the magnitude of the current, induced by magnetic-resonance imaging, flowing through the tissue at a distal end of a medical device using the bipolar pacing lead circuit of FIG. 14 using an increased resistance in the resonant circuit.

FIG. 16, it is assumed that the bipolar pacing leads of FIG. 14 are subjected to a magnetic resonance imaging environment wherein the resistance of the current limiting resistor 5130 is increased. As demonstrated in FIG. 16, the current (IRt1, which represents the current flowing through tissue modeled resistor 1230 of FIG. 14) induced by the magnetic resonance imaging environment and flowing through the tissue at the distal end of the second bipolar pacing lead 1200 can be reduced, but the increased resistance of the current limiting resistor 5130 has a slight negative impact on the effectiveness of the resonant circuit 5000. It is noted that the current (IRt2, which represents the current flowing through tissue modeled resistor 1130 of FIG. 14) induced by the magnetic resonance imaging environment and flowing through the tissue at the distal end of the first bipolar pacing lead 1100 can have a magnitude between 1.21 and −1.21 amps. This reduced magnitude of current (IRt1, which represents the current flowing through tissue modeled resistor 1230 of FIG. 14) at the distal end of the bipolar pacing lead can significantly reduce the damage to the tissue due to heat generated by the current flowing to the tissue. It is noted that the current ILFilter1 through the inductor 5110 has decreased with the increase in the resistance of resistor 5130, thereby illustrating controlling the current through the inductor 5110 of the resonant circuit.

It is noted that the frequencies used in generating the various graphs are examples and do not represent the exact frequencies to be used in the design and manufacturing of these circuits. More specifically, the exact frequencies to be used are governed by the Larmor frequency of the proton in the Hydrogen atom and the frequency of the radio frequency of the magnetic resonance imaging scanner.

The gyromagnetic ratio for the proton in the Hydrogen atom is γ=42.57 MHz/T or γ=42.58 MHz/T, depending on the reference used. In the following discussion γ=42.57 MHz/T will be used.

Given that the Larmor equation is $f=B_0 \times \gamma$, the frequency to which the resonant circuit is to be tuned, for example, in a 1.5 T magnetic resonance imaging scanner, is $f=(1.5\ T)(42.57\ MHz/T)=63.855$ MHz.

The following table gives the resonance frequency for several cases along with example circuit parameter values for the inductor and capacitor to form the resonance circuit.

TABLE 1

| $B_0$ (Tesla) | Circuit Resonance Frequency (MHz) | Example Circuit Parameters ||
|---|---|---|---|
| | | Inductor (nH) | Capacitor (pF) |
| 0.5 | 21.285 | 50 | 1118.2 |
| 1.0 | 42.57 | 50 | 279.55 |
| 1.5 | 63.855 | 50 | 124.245 |
| 3.0 | 127.71 | 50 | 31.06 |

These circuit parameter values are for the ideal case. So, it is expected that the actual values used in a real circuit could be different. That is, in the excitation signal's frequency environment of the magnetic resonance imaging scanner, there are other effects (like parasitic capacitance in the inductor) that may affect the circuit, requiring the circuit parameters to be adjusted.

It is noted that introducing the resonant circuit only into one of the two bipolar pacing wires may result in an increase in the current through the other wire.

Figure 17:
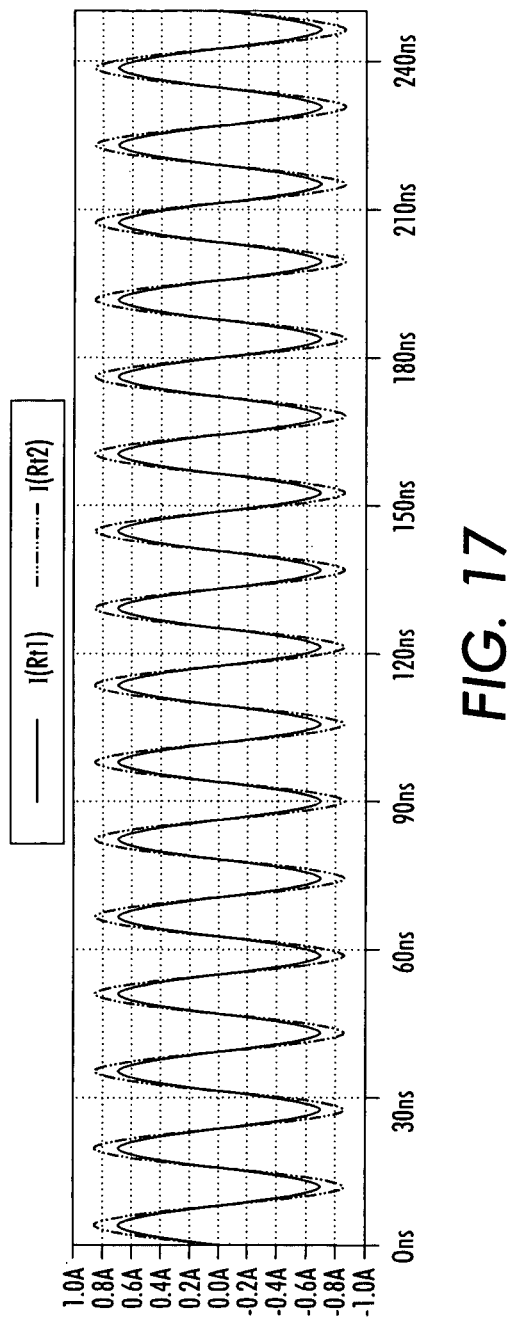
FIG. 17 is a graph illustrating the magnitude of the current, induced by magnetic-resonance imaging, flowing through the tissue at a distal end of a medical device using a conventional bipolar pacing lead circuit.

For example, as illustrated in FIG. 17, when no resonant circuits are included with the bipolar pacing leads (FIG. 2), the current flowing through the first tissue modeled resistor 130 and second tissue modeled resistor 230 of FIG. 2 is significant, thereby generating heat to possibly damage the tissue.

Figure 18:
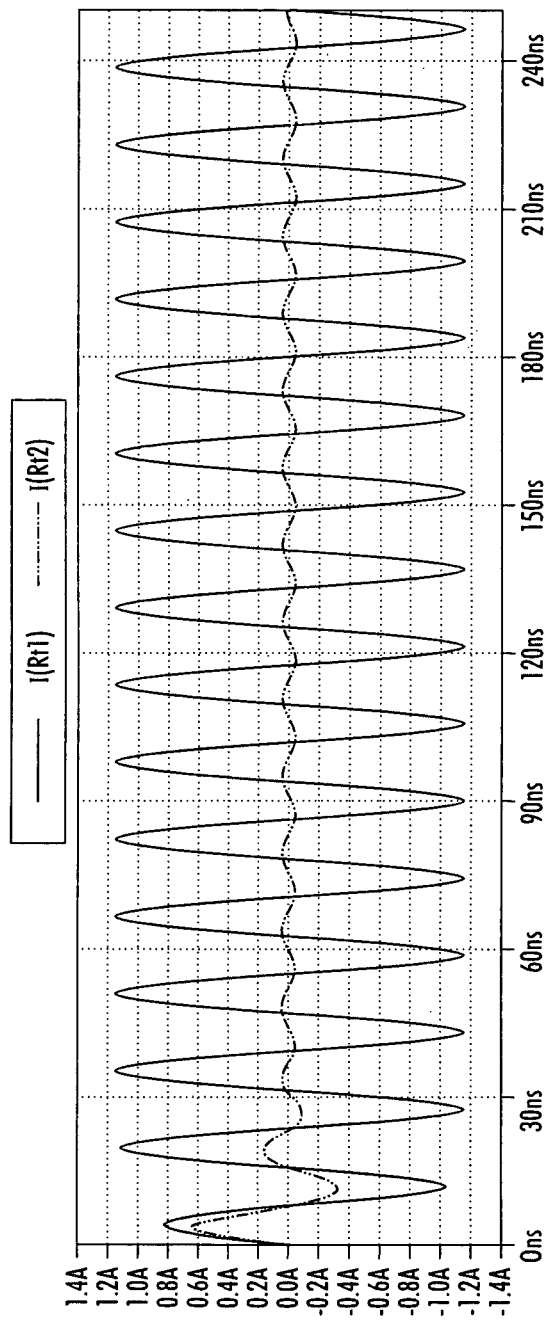
FIG. 18 is a graph illustrating the magnitude of the current, induced by magnetic-resonance imaging, flowing through the tissue at a distal end of a medical device using the bipolar pacing lead circuit with a resonant circuit in one lead.

On the other hand, as illustrated in FIG. 18, when a resonant circuit or resonant circuits are included in only one of the bipolar pacing leads (FIGS. 4, 7, 10 and 14), the current (IRt1) flowing through the second tissue modeled resistor 1230 is significantly reduced in the one lead, but the current (IRt2) slightly increases in the first tissue modeled resistor 1130. It is noted that these behaviors are dependent on the characteristics of the implemented pacing lead and pulse generator system.

Figure 19:
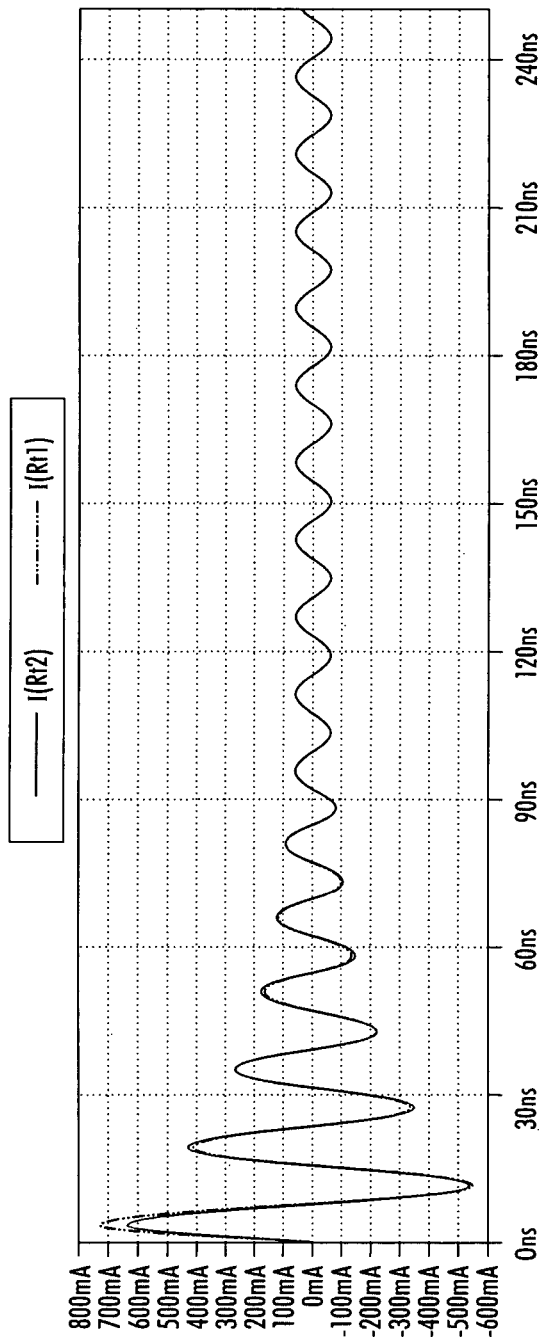
FIG. 19 is a graph illustrating the magnitude of the current, induced by magnetic-resonance imaging, flowing through the tissue at a distal end of a medical device using the bipolar pacing lead circuit with a resonant circuit in both leads.

On the other hand, as illustrated in FIG. 19, when a resonant circuit or resonant circuits are included in both bipolar leads (not shown), the current (IRt1 and IRt2) flowing through the tissue modeled resistors 130 and 1130 and second tissue modeled resistor 230 and 1230 is significantly reduced.

It is noted that even if the resonant circuits of the present invention are tuned, for example to 63.86 MHz on the bench top, when the resonant circuits of the present invention are placed in the patient's body, the resonant circuits of the present invention may shift resonance a little because of inductive and capacitive coupling to the surrounding environment.

Figure 20:
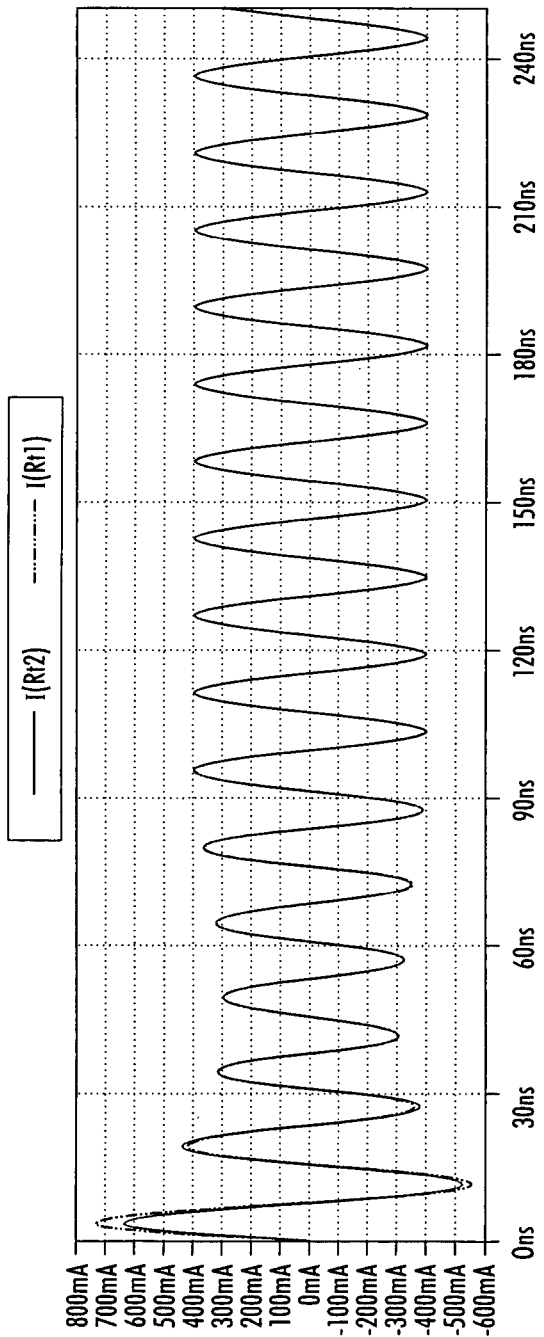
FIG. 20 is a graph illustrating the magnitude of the current, induced by magnetic-resonance imaging, flowing through the tissue at a distal end of a medical device using the bipolar pacing lead circuit with a resonant circuit in both leads and increased inductance.
Figure 21:
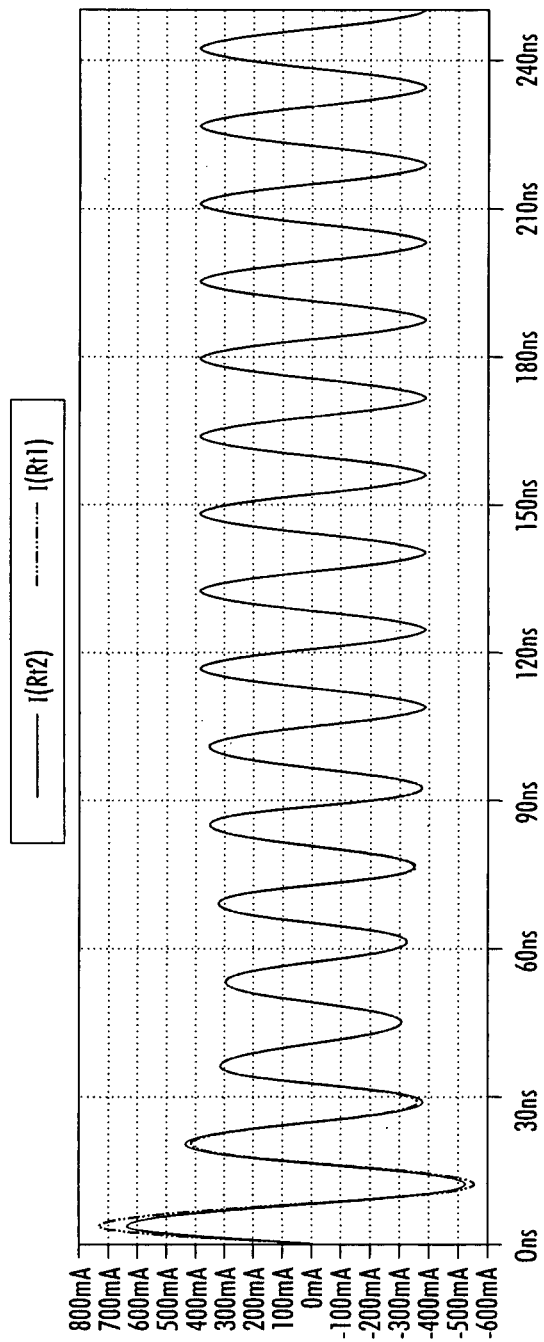
FIG. 21 is a graph illustrating the magnitude of the current, induced by magnetic-resonance imaging, flowing through the tissue at a distal end of a medical device using the bipolar pacing lead circuit with a resonant circuit in both leads and decreased inductance.

Notwithstanding the potential shift, the concepts of the present invention still significantly reduce the heat generated current in the tissue at the distal end of the bipolar pacing leads, as illustrated in FIGS. 20 and 21. FIGS. 20 and 21 provide a graphical representation of the effectiveness of the resonant circuits of the present invention as the circuits are tuned away from the ideal resonance of 63.86 MHz (for the 1.5 T case).

In FIG. 20, the inductance of the resonant circuit is increased by 10%. In this instance, the resonant circuits of the present invention significantly reduce the heat generated by currents (IRt1 and IRt2) in the tissue at the distal end of the bipolar pacing leads.

Moreover, in FIG. 21, the inductance of the resonant circuit is decreased by 10%. In this instance, the resonant circuits of the present invention significantly reduce the heat generated by currents (IRt1 and IRt2) in the tissue at the distal end of the bipolar pacing leads.

Therefore, the resonant circuits of the present invention need not be perfectly tuned to be effective. As mentioned above, even if the resonant circuits of the present invention were perfectly tuned, once implanted into a patient, the circuits are expected to shift resonance frequency a little bit.

Figure 22:
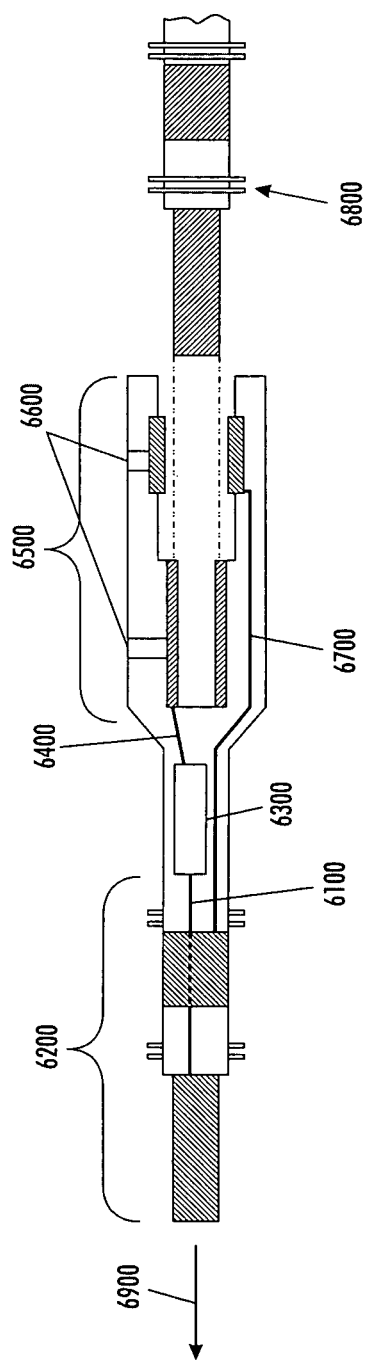
FIG. 22 shows a bipolar pacing lead adaptor with a single resonant circuit according to some or all of the concepts of the present invention.

FIG. 22 illustrates an adapter which can be utilized with an existing conventional bipolar pacing lead system. As illustrated in FIG. 22, an adapter 6000 includes a male IS-1-BI connector 6200 for providing a connection to an implantable pulse generator 6900. The adapter 6000 includes a female IS-1-BI connector 6500 for providing a connection to bipolar pacing lead 6800. The female IS-1-BI connector 6500 includes locations 6600 for utilizing set screws to hold the adapter 6000 to the bipolar pacing lead 6800.

The adapter 6000 further includes connection wire 6700 to connect the outer ring of the bipolar pacing lead 6800 to the outer ring of the implantable pulse generator 6900. The adapter 6000 includes a wire 6400 to connect an inner ring of the bipolar pacing lead 6800 to a resonant circuit 6300 and a wire 6100 to the resonant circuit 6300 to an inner ring of the implantable pulse generator 6900. It is noted that an additional resonant circuit could be placed between the outer ring of the bipolar pacing lead 6800 and the outer ring of the implantable pulse generator 6900.

It is noted that the resonant circuit 6300 in FIG. 22 can be multiple resonant circuits in series. It is also noted that the adaptor 6000 can be manufactured with resonant circuits in series with both wires of the bipolar pacing lead. It is further noted that this adapter is connected to the proximal end of the bipolar pacing lead.

Additionally, the adapter of the present invention may include enough mass in the housing to dissipate the heat generated by the resonant circuits. Alternatively, the adapter may be constructed from special materials; e.g., materials having a thermal transfer high efficiency, etc.; and/or structures; e.g., cooling fins, etc.; to more effectively dissipate the heat generated by the resonant circuits. Furthermore, the adapter may include, within the housing, special material; e.g., materials having a thermal transfer high efficiency, etc.; and/or structures; e.g., cooling fins, etc.; around the resonant circuits to more effectively dissipate the heat generated by the resonant circuits.

The concepts of the adapter of FIG. 22 can be utilized in a different manner with an existing conventional bipolar pacing lead system. For example, an adapter may include a connector for providing a connection to an implantable electrode or sensor. On the other hand, the adapter may include an implantable electrode or sensor instead a connection for the electrode or sensor.

The adapter may also include a connector for providing a connection to bipolar pacing lead. The connector may include locations for utilizing set screws or other means for holding the adapter to the bipolar pacing lead.

As in FIG. 22, this modified adapter would include a connection wire to connect one conductor of the bipolar pacing lead to the electrode or sensor. The modified adapter would include a wire to connect the other conductor of the bipolar pacing lead to a resonant circuit and a wire to the resonant circuit to ring associated with the electrode of other device associated with the sensor, such as a ground. It is noted that an additional resonant circuit could be placed between the conductor of the bipolar pacing lead and the electrode or sensor.

It is noted that the resonant circuit can be multiple resonant circuits in series. It is also noted that the modified adaptor can be manufactured with resonant circuits in series with both wires of the bipolar pacing lead. It is further noted that this modified adapter is connected to the distal end of the bipolar pacing lead.

Additionally, the modified adapter of the present invention may include enough mass in the housing to dissipate the heat generated by the resonant circuits. Alternatively, the modified adapter may be constructed from special materials; e.g., materials having a thermal transfer high efficiency, etc.; and/or structures; e.g., cooling fins, etc.; to more effectively dissipate the heat generated by the resonant circuits. Furthermore, the modified adapter may include, within the housing, special material; e.g., materials having a thermal transfer high efficiency, etc.; and/or structures; e.g., cooling fins, etc.; around the resonant circuits to more effectively dissipate the heat generated by the resonant circuits.

It is noted that all other wires and electrodes which go into a magnetic resonance imaging environment, (and not necessarily implanted into the patient's body) can be augmented with a resonant circuit. Any wires to sensors or electrodes, like the electrodes of EEG and EKG sensor pads, can be augmented with a resonant circuit in series with their wires. Even power cables can be augmented with resonant circuits.

Other implanted wires, e.g. deep brain stimulators, pain reduction stimulators, etc. can be augmented with a resonant circuit to block the induced currents caused by the excitation signal's frequency of the magnetic resonance imaging scanner.

Additionally, the adapter of the present invention, when used within implanted devices, may contain means for communicating an identification code to some interrogation equipments external to the patient's body. That is, once the implantable pulse generator, adapter, and pacing lead are implanted into the patient's body, the adapter has means to communicate and identify itself to an external receiver. In this way, the make, model, year, and the number of series resonance circuits can be identified after it has been implanted into the body. In this way, physicians can interrogate the adapter to determine if there is a resonance circuit in the adapter which will block the excitation signal's frequency induced currents caused by the magnetic resonance imaging scanner the patient is about to be placed into.

Furthermore, the adapter of the present invention has the capability of being tested after implantation to insure that the resonance circuit is functioning properly.

Since the present invention is intended to be used in a magnetic resonance imaging scanner, care needs to be taken when selecting the inductor to be used to build the resonant circuit. The preferred inductor should not contain a ferromagnetic or ferrite core. That is, the inductor needs to be insensitive to the magnetic resonance imaging scanner's $B_0$ field. The inductor should also be insensitive to the excitation signal's frequency field (B1) of the magnetic resonance imaging scanner. The inductor should function the same in any orientation within the magnetic resonance imaging scanner. This might be accomplished putting the inductor (for the entire resonant circuit) in a Faraday cage.

Figure 23:
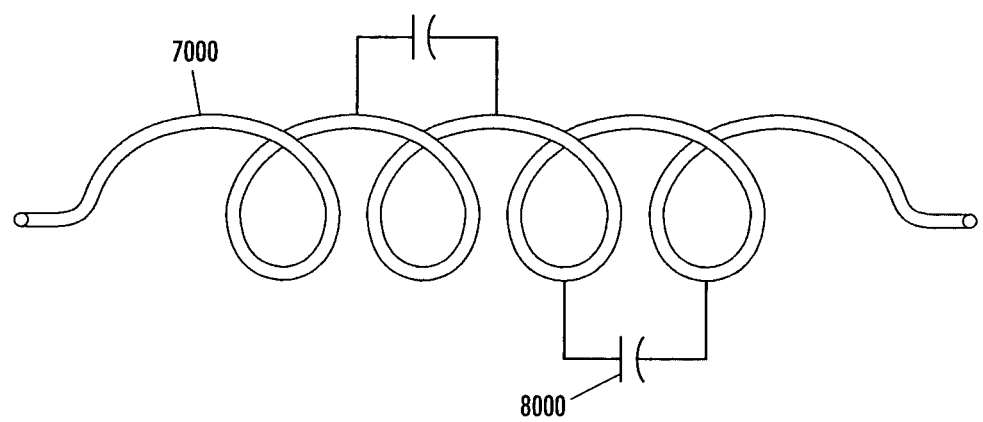
FIG. 23 illustrates a resonant circuit for a bipolar pacing lead according to some or all of the concepts of the present invention.

The resonant circuit of the present invention could also be realized by adding capacitance along the bipolar pacing lead, as illustrated in FIG. 23. In FIG. 23, capacitors 8000 are added across the coils of the pacing lead 7000.

As illustrated in FIG. 23, an oxidation layer or an insulating material is formed on the wire resulting in essentially a resistive coating over the wire form. Thus, the current does not flow through adjacent coil loop contact points, but the current instead follows the curvature of the wire. The parasitic capacitance enables electrical current to flow into and out of the wire form due to several mechanisms, including the oscillating electrical field set up in the body by the magnetic resonance imaging unit.

In pacing leads and some other leads, a coiled wire is used. A thin insulative film (polymer, enamel, etc.) is coated over the wire (or a portion thereof) used to electrically insulate one coiled loop from its neighboring loops. This forms an inductor. By inserting an appropriate sized capacitor 8000 across multiple loops of the coiled wire (or a portion thereof), a parallel resonance circuit suitable for reducing the induced current, in accordance with the concepts of the present invention, can be formed.

Figure 24:
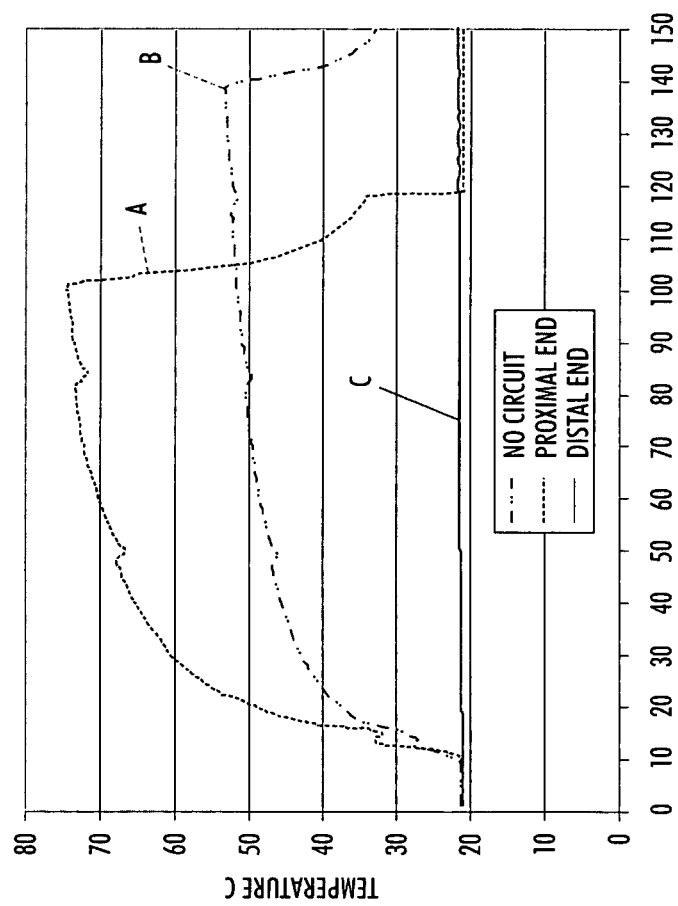
FIG. 24 is a graph illustrating the temperature at a distal end of a medical device.

FIG. 24 shows the temperature of the tissue at the distal end of a wire wherein the wire includes a resonant circuit at the proximal end (A); the wire does not include a resonant circuit (B); and the wire includes a resonant circuit at the distal end (C).

As illustrated in FIG. 24, the "Proximal End" case (A) (resonant circuit at proximal end) results in a higher temperature increase at the distal end than when the resonant circuit is located at the distal end (C). In the demonstration used to generate the results of FIG. 24, a wire of 52 cm in length and having a cap at one end was utilized, resulting in a distributive capacitive coupling to the semi-conductive fluid into which the wires were placed for these magnetic resonance imaging heating experiments.

For the "Proximal End" case (A) (resonant circuit at proximal end) only, the resonant circuit was inserted 46.5 cm along the wire's length. Since no current at 63.86 MHz can pass through the resonant circuit, this sets any resonant wave's node at 46.5 cm along the wire. This effectively shortened the length of the wire and decreased the wire's self-inductance and decreased the distributive capacitance. These changes then "tuned" the wire to be closer to a resonance wave length of the magnetic resonance imaging scanner's transmitted radio frequency excitation wave resulting in an increase in the current at the distal end of the wire.

Figure 25:
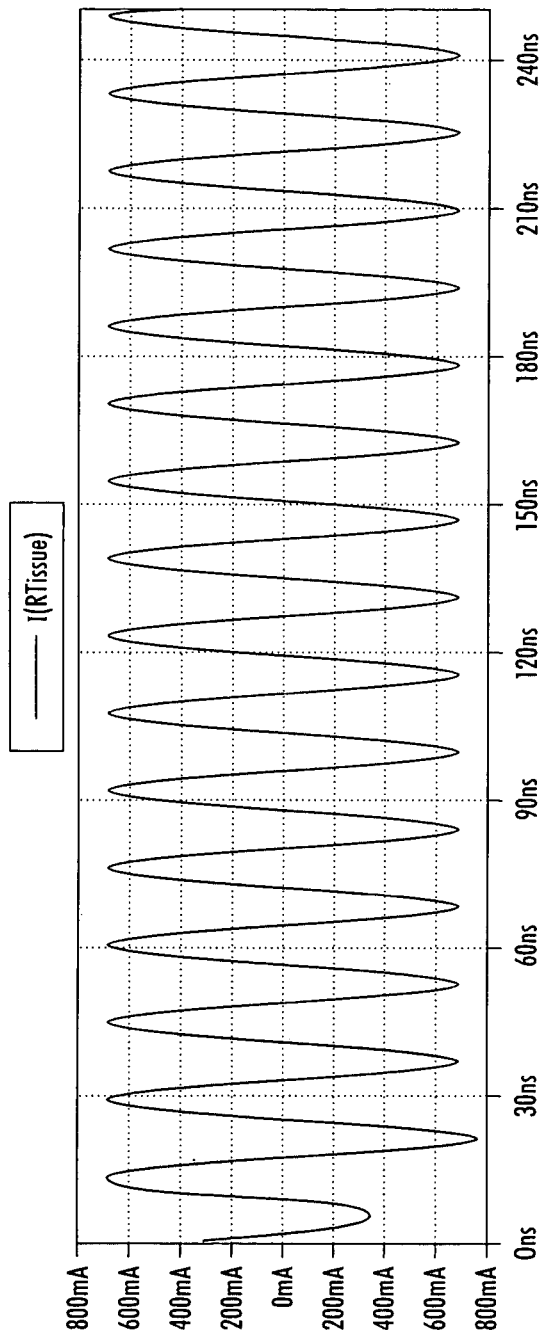
FIG. 25 is a graph illustrating the magnitude of the current, induced by magnetic-resonance imaging, flowing through the tissue at a distal end of a conventional medical device.
Figure 26:
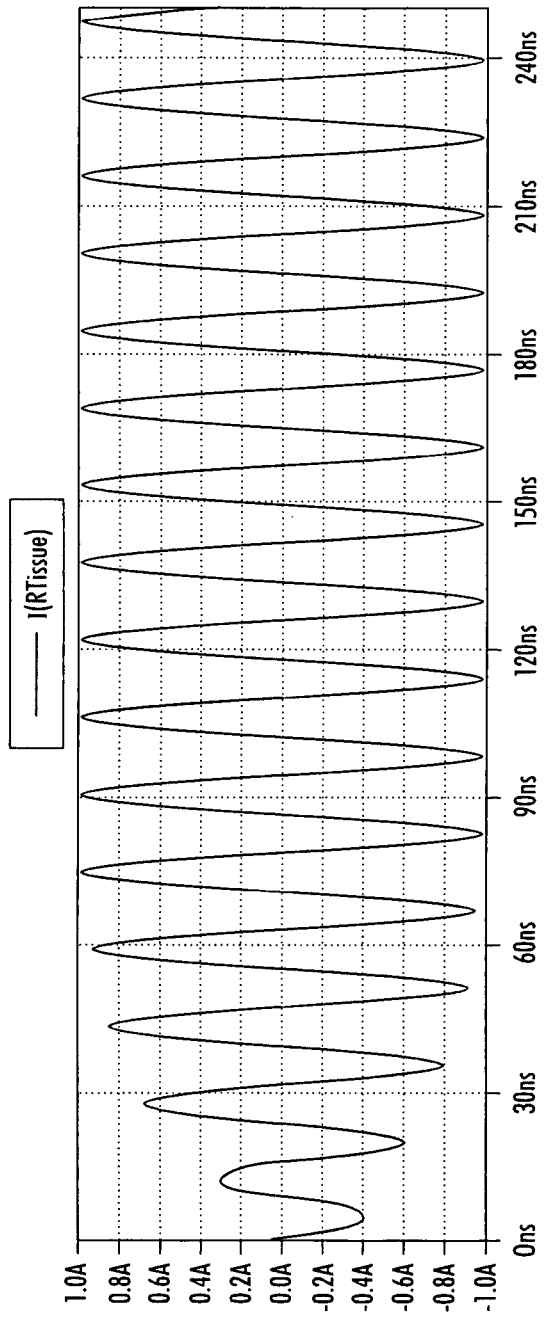
FIG. 26 is a graph illustrating the magnitude of the current, induced by magnetic-resonance imaging, flowing through the tissue at a distal end of a medical device with a resonant circuit, according to the concepts of the present invention, at the proximal end thereof.

The effective length of the wire with the resonant circuit is now 46.5 cm rather than the physical length of 52 cm. That is, the inductance and capacitance of the wire is now such that its inherent resonance frequency is much closer to that of the applied radio-frequency. Hence, the modeled current through the distal end into the surrounding tissue increases from about 0.65 Amps when there is no resonant circuit at the proximal end (FIG. 25) to about 1.0 Amps when the resonant circuit is inserted at the proximal end of the wire (FIG. 26).

Figure 27:
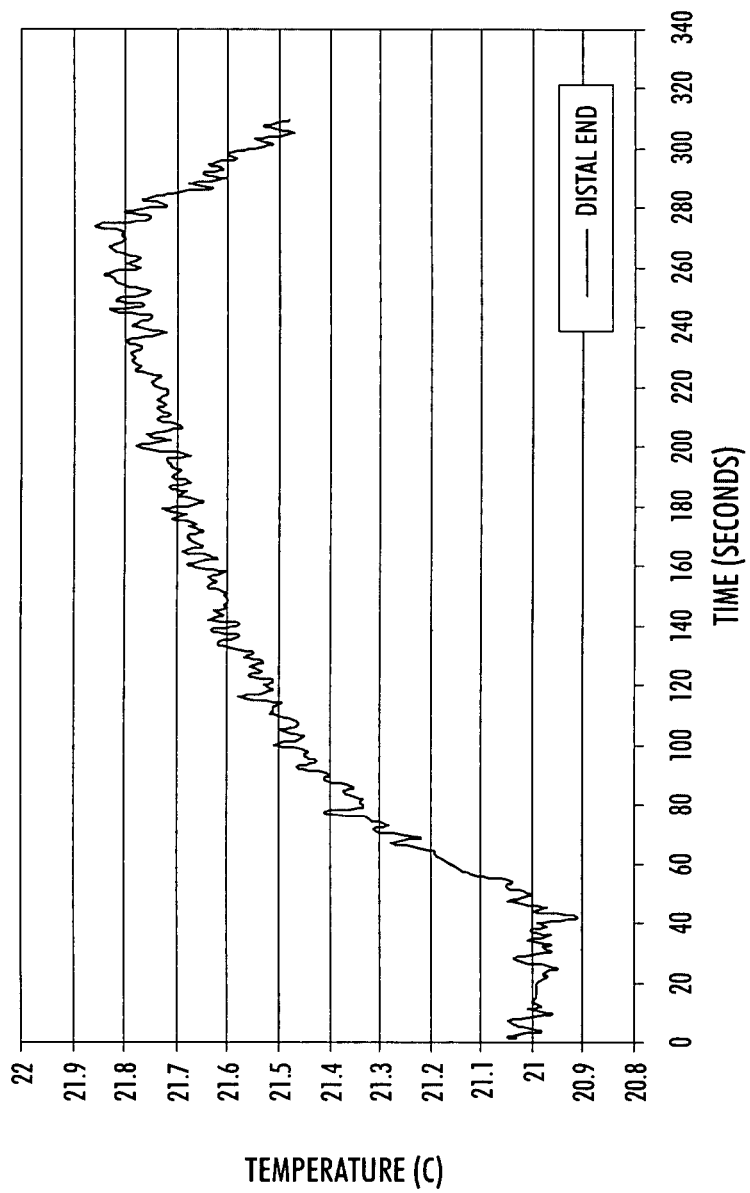
FIG. 27 is a graph illustrating the temperature at a distal end of a medical device with a resonant circuit, according to the concepts of the present invention, at the distal end thereof.

As illustrated in FIG. 27 (which is a close up of trace "C" in FIG. 24), when the wire includes a resonant circuit at the distal end, the temperature rise is significantly less (about 0.9° C. after 3.75 minutes). On the other hand, when the wire includes a resonant circuit at the proximal end, the temperature rise at the distal end is greater (See trace "A" in FIG. 24).

Figure 28:
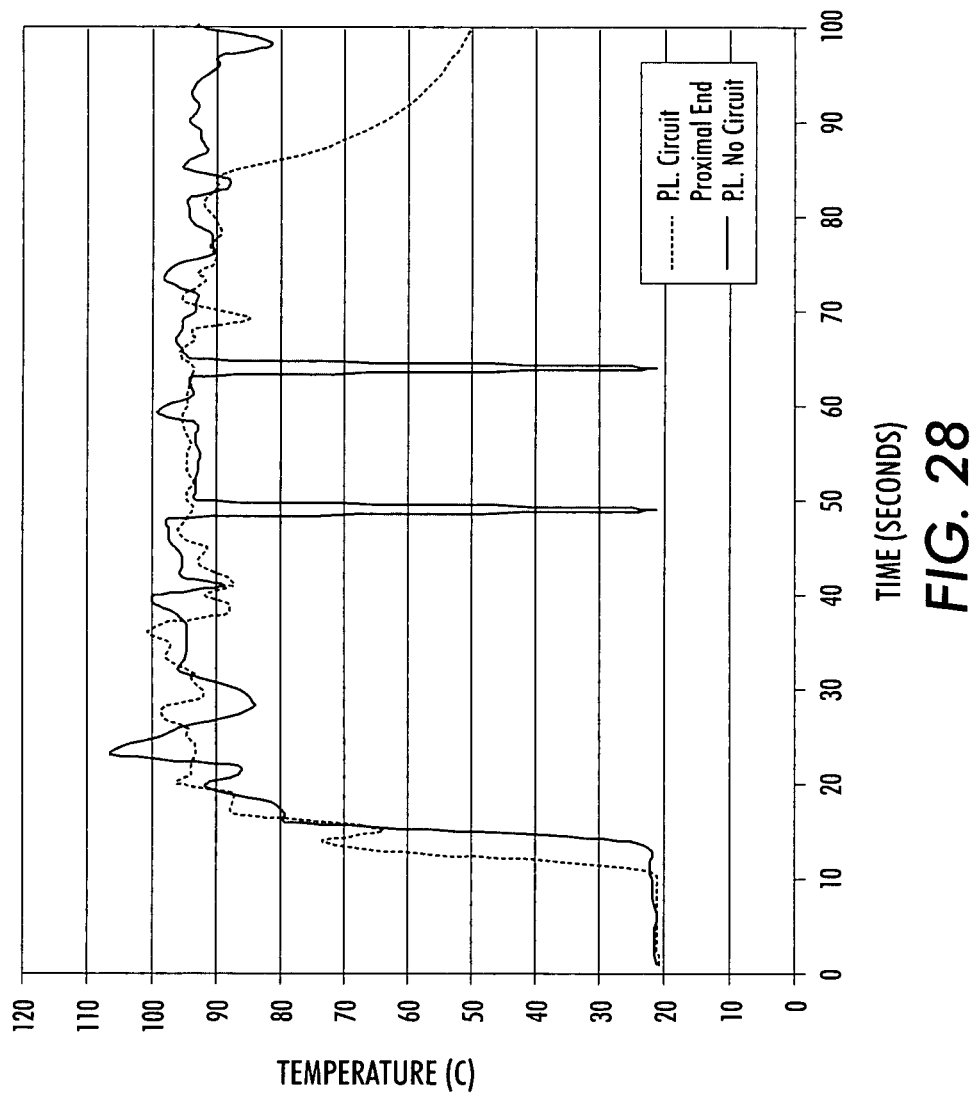
FIG. 28 is a graph illustrating the temperature at a distal end of a medical device with a resonant circuit, according to the concepts of the present invention, at the proximal end thereof.

Experimental results with the resonant circuit at the proximal end of a 52 cm long bipolar pacing lead did not demonstrate a significant altering of the heating of the tissue at the distal end, as illustrated in FIG. 28. The attachment of the resonant circuit to the proximal end of a pacing lead places a wave node at the end of the pacing lead (no real current flow beyond the end of wire, but there is a displacement current due to the capacitance coupling to the semi-conductive fluid). That is, adding the resonant circuit to the proximal end of the pacing lead, which does not change the effective length of the pacing lead, does not change the electrical behavior of the pacing lead.

Now referring back to FIG. 15, it is noted that the current (Lfilter1) through the resonant circuit inductor 5110 of FIG. 14 is also illustrated. As can be seen, the current (Lfilter1) through the resonant circuit inductor 5110 of FIG. 14 is larger than the original current passing through a prior art lead, as illustrated in FIG. 3. Although the heating of the tissue is significantly decreased with the addition of a resonant circuit, there still may be a problem in that inductors is rated for a certain amount of current before the inductor is damaged.

In anticipation of a possible problem with using inductors not having a high enough current rating, the present invention may provide multiple resonant circuits, each resonant circuit being connected in series therewith and having the same inductor and capacitor (and resistor) value as the original resonant circuit.

As noted above, FIG. 7 illustrates an example of multiple serially connected resonant circuits. Although previously described as having values to create different resonance values, the resonant circuits 2000 and 3000 of FIG. 7 may also have substantially the same resonance values so as to reduce the current flowing through any single inductor in the resonant circuits 2000 and 3000 of FIG. 7.

Moreover, in anticipation of a possible problem with using inductors not having a high enough current rating, the present invention may provide resonant circuits with inductors having larger inductive values. It is noted that it may be difficult to implement an inductor having a larger inductive value in a small diameter lead, such as a pacing lead or DBS lead. In such a situation, the inductor may be constructed to be longer, rather than wider, to increase its inductive value.

It is further noted that the resonance values of the resonant circuits 2000 and 3000 of FIG. 7 may be further modified so as to significantly reduce the current through the tissue as well as the current through the resonant circuit's inductor. More specifically, the multiple resonant circuits may be purposely tuned to be off from the operating frequency of the magnetic resonance imaging scanner. For example, the resonance frequency of the resonant circuit may be 70.753 MHz or 74.05 MHz.

In this example, when one resonant circuit of the multiple resonant circuits is purposely not tuned to the operating frequency of the magnetic resonance imaging scanner, the current through the tissue is reduced, while the current through the resonant circuit's inductor is also reduced. Moreover, when two resonant circuits of the multiple resonant circuits are purposely not tuned to the operating frequency of the magnetic resonance imaging scanner, the current through the tissue is further reduced, while the current through the resonant circuit's inductor is also further reduced.

It is further noted that when the two (or more) resonant circuits are not tuned exactly to the same frequency and all the resonant circuits are not tuned to the operating frequency of the magnetic resonance imaging scanner, there is significant reduction in the current through the tissue as well as the current through the resonant circuits' inductors.

In summary, putting the resonant circuit at the proximal end of a pacing lead does not reduce the heating at the distal end of the pacing. However, placing the resonant circuit at the proximal end of the pacing lead can protect the electronics in the implanted pulse generator which is connected at the proximal end. To protect the circuit in the implanted pulse generator, a resonant circuit is placed at the proximal end of the pacing lead so as to block any induced currents from passing from the pacing lead into the implanted pulse generator.

Since the current in the resonant circuit, when in the magnetic resonance imaging scanner (or other radio-frequency field with a frequency of the resonant frequency of the circuit) may be larger than the induced current in the lead (or wire) without the resonant circuit, there may be some heating in the resistive elements of the resonant circuit (in the wires, connection methods, inductor, etc.). Thus, it would be advantageous to connect high thermal conductive material to the resonant circuit to distribute any heating of the circuit over a larger area because heating is tolerable when it is not concentrated in one small place. By distributing the same amount of heating over a larger area, the heating problem is substantially eliminated.

To distribute the heat, the inside of the pacing lead polymer jacket can be coated with a non-electrical conductive material which is also a very good thermal conductor and this connected to the circuit. Moreover, filaments of non-electrically conductive but thermally conductive material can be attached to the circuit and run axially along the inside of the pacing lead assembly.

As discussed above, a lead may include a conductor having a distal end and a proximal end and a resonant circuit connected to the conductor. The resonant circuit has a resonance frequency approximately equal to an excitation signal's frequency of a magnetic-resonance imaging scanner. The resonant circuit may be located at the distal end of the conductor or the proximal end of the conductor. The resonant circuit may be an inductor connected in parallel with a capacitor or an inductor connected in parallel with a capacitor and a resistor, the resistor and capacitor being connected in series.

It is noted that a plurality of resonant circuits may be connected in series, each having a unique resonance frequency to match various types of magnetic-resonance imaging scanners or other sources of radiation, such as security systems used to scan individuals for weapons, etc. It is further noted that the lead may include a heat receiving mass located adjacent the resonant circuit to dissipate the heat generated by the resonant circuit in a manner that is substantially non-damaging to surrounding tissue. Furthermore, it is noted that the lead may include a heat dissipating structure located adjacent the resonant circuit to dissipate the heat generated by the resonant circuit in a manner that is substantially non-damaging to surrounding tissue.

It is also noted that the above described lead may be a lead of a bipolar lead circuit.

Moreover, as discussed above, an adapter for a lead may include a housing having a first connector and a second connector, the first connector providing a mechanical and electrical connection to a lead, the second connector providing a mechanical and electrical connection to a medical device, and a resonant circuit connected to the first and second connectors. The resonant circuit may have a resonance frequency approximately equal to an excitation signal's frequency of a magnetic-resonance imaging scanner. The resonant circuit may be an inductor connected in parallel with a capacitor or an inductor connected in parallel with a capacitor and a resistor, the resistor and capacitor being connected in series.

It is noted that a plurality of resonant circuits may be connected in series, each having a unique resonance frequency to match various types of magnetic-resonance imaging scanners or other sources of radiation, such as security systems used to scan individuals for weapons, etc. It is further noted that the adapter may include a heat receiving mass located adjacent the resonant circuit to dissipate the heat generated by the resonant circuit in a manner that is substantially non-damaging to surrounding tissue. Furthermore, it is noted that the adapter may include a heat dissipating structure located adjacent the resonant circuit to dissipate the heat generated by the resonant circuit in a manner that is substantially non-damaging to surrounding tissue.

Furthermore, as discussed above, medical device may include a housing having electronic components therein; a lead mechanically connected to the housing and electrically connected through the housing; and a resonant circuit, located within the housing, operatively connected to the lead and the electronic components. The resonant circuit may have a resonance frequency approximately equal to an excitation signal's frequency of a magnetic-resonance imaging scanner. The resonant circuit may be an inductor connected in parallel with a capacitor or an inductor connected in parallel with a capacitor and a resistor, the resistor and capacitor being connected in series.

It is noted that a plurality of resonant circuits may be connected in series, each having a unique resonance frequency to match various types of magnetic-resonance imaging scanners or other sources of radiation, such as security systems used to scan individuals for weapons, etc. It is further noted that the adapter may include a heat receiving mass located adjacent the resonant circuit to dissipate the heat generated by the resonant circuit in a manner that is substantially non-damaging to surrounding tissue. Furthermore, it is noted that the adapter may include a heat dissipating structure located adjacent the resonant circuit to dissipate the heat generated by the resonant circuit in a manner that is substantially non-damaging to surrounding tissue.

It is noted that although the various embodiments have been described with respect to a magnetic-resonance imaging scanner, the concepts of the present invention can be utilized so as to be tuned to other sources of radiation, such as security systems used to scan individuals for weapons, etc. In these instances, the frequency of an electromagnetic radiation source is the "normal" frequency of an electromagnetic wave. Even if the electromagnetic wave is "circularly polarized", it is not the circular frequency, but the "normal" frequency.

While various examples and embodiments of the present invention have been shown and described, it will be appreciated by those skilled in the art that the spirit and scope of the present invention are not limited to the specific description and drawings herein, but extend to various modifications and changes thereof.

What is claimed is:

1. An implantable adapter for coupling an implantable lead to an implantable medical device, the adapter comprising:
   a housing of the implantable adapter configured at a first end to form a first mechanical connector to provide a reversible mechanical connection to a proximal end of the implantable lead and configured at a second end to form a second mechanical connector to provide a reversible mechanical connection to the implantable medical device, wherein the implantable medical device comprises an implantable medical device housing separate from the housing of the implantable adapter;
   a first resonant circuit within the housing of the implantable adapter, the first resonant circuit having a resonance frequency approximately equal to a frequency of a first electromagnetic radiation source;
   a second resonant circuit within the housing of the implantable adapter and connected in series with the first resonant circuit, the second resonant circuit having a resonance frequency approximately equal to a frequency of a second electromagnetic radiation source;

a first wire within the housing of the implantable adapter to electrically connect a first wire of the implantable lead to the first resonant circuit; and a second wire within the housing of the implantable adapter to electrically connect the second resonant circuit to the implantable medical device.

2. The implantable adapter as claimed in claim 1, wherein said first resonant circuit is an inductor connected in parallel with a capacitor.

3. The implantable adapter of claim 1, wherein said first resonant circuit is an inductor connected in parallel with a capacitor and a resistor, said resistor and capacitor being connected in series.

4. The implantable adapter as claimed in claim 1, further comprising: a heat dissipating structure; said heat dissipating structure being located adjacent to said first resonant circuit; said heat dissipating structure dissipating the heat generated by said first resonant circuit.

5. The implantable adapter as claimed in claim 1, wherein said second resonant circuit is an inductor connected in parallel with a capacitor.

6. The implantable adapter of claim 1, wherein said second resonant circuit is an inductor connected in parallel with a capacitor and a resistor, said resistor and capacitor being connected in series.

7. The implantable adapter as claimed in claim 1, further comprising: a heat dissipating structure; said heat dissipating structure being located adjacent to said second resonant circuit; said heat dissipating structure dissipating the heat generated by said second resonant circuit.

8. The adapter of claim 1, wherein the first mechanical connector comprises a female connector and the second mechanical connector comprises a male connector.

9. The adapter of claim 1, further comprising a third wire within the housing of the adapter that electrically connects a second wire of the implantable lead to the implantable medical device.

10. An adapter for coupling an implantable lead to an implantable medical device, the adapter comprising:

a housing of the adapter configured at a first end to form a first mechanical connector to provide a reversible mechanical connection to a proximal end of the implantable lead and configured at a second end to form a second mechanical connector to provide a reversible mechanical connection to the implantable medical device, wherein the implantable medical device comprises an implantable medical device housing separate from the housing of the implantable adapter;

a first resonant circuit within the housing of the adapter, the first resonant circuit having a resonance frequency approximately equal to a frequency of an electromagnetic radiation source;

a second resonant circuit within the housing of the adapter, the second resonant circuit having a resonance frequency approximately equal to the frequency of the electromagnetic radiation source;

a first wire within the housing of the adapter to electrically connect a first wire of the implantable lead to the first resonant circuit; and a second wire within the housing of the adapter to electrically connect the first resonant circuit to the implantable medical device;

a third wire within the housing of the adapter to electrically connect a second wire of the implantable lead to the second resonant circuit; and a fourth wire within the housing of the adapter to electrically connect the second resonant circuit to the implantable medical device.

11. The adapter of claim 10, further comprising a third resonant circuit within the housing of the adapter, wherein the third resonant circuit is connected in series with the first resonant circuit, the third resonant circuit having a resonance frequency approximately equal to a frequency of a second electromagnetic source that is different than the frequency of the first electromagnetic source.

12. The adapter of claim 10, wherein at least one of the said first resonant circuit and said second resonant circuit is an inductor connected in parallel with a capacitor.

13. The adapter of claim 10, wherein at least one of the said first resonant circuit and said second resonant circuit is an inductor connected in parallel with a capacitor and a resistor, said resistor and capacitor being connected in series.

14. The adapter of claim 10, further comprising a heat dissipating structure, said heat dissipating structure being located adjacent to the first resonant circuit and dissipating heat generated by the first resonant circuit.

15. The adapter of claim 14, wherein the heat dissipating structure includes one or more cooling fins.

16. The adapter of claim 10, wherein the first connector comprises a female mechanical connector and the second mechanical connector comprises a male connector.

17. An implantable medical system comprising:

an implantable medical device having a female connector, wherein the implantable medical device comprises an implantable medical device housing;

an implantable medical lead having a male connector; and an adapter for electrically coupling the implantable medical lead to the implantable medical device, the adapter comprising:

a housing of the adapter configured at a first end to form a female connector to provide a reversible mechanical connection to the male connector of the implantable medical lead and configured at a second end to form a male connector to provide a reversible mechanical connection to the female connector of the implantable medical device, wherein the housing of the adapter is separate from the implantable medical device housing;

a first resonant circuit within the housing of the adapter, the first resonant circuit having a resonance frequency approximately equal to a frequency of a first electromagnetic radiation source;

a second resonant circuit within the housing of the adapter and in series with the first resonant circuit, the second resonant circuit having a resonance frequency approximately equal to a frequency of a second electromagnetic radiation source;

a first wire within the housing of the adapter to electrically connect a first wire of the implantable lead to the first resonant circuit; and a second wire within the housing of the adapter to electrically connect the second resonant circuit to the implantable medical device.

18. The adapter of claim 17, further comprising a third wire within the housing of the adapter that electrically connects a second wire of the implantable lead to the implantable medical device.

* * * * *